(12) United States Patent
Dash et al.

(10) Patent No.: US 10,046,318 B2
(45) Date of Patent: Aug. 14, 2018

(54) LIGAND COMPONENTS, ASSOCIATED REACTION PRODUCTS, ACTIVATED REACTION PRODUCTS, HYDROSILYLATION CATALYSTS AND HYDROSILYLATION CURABLE COMPOSITIONS INCLUDING THE LIGAND COMPONENTS, AND ASSOCIATED METHODS FOR PREPARING SAME

(71) Applicants: DOW CORNING CORPORATION, Midland, MI (US); THE BOARD OF TRUSTEES OF THE UNIVERSITY OF ILLINOIS, Champaign, IL (US)

(72) Inventors: Aswini Dash, Midland, MI (US); Thomas B. Rauchfuss, Urbana, IL (US); Wan-Yi Chu, Champaign, IL (US); Ryan J. Gilbert-Wilson, Urbana, IL (US)

(73) Assignees: DOW SILICONES CORPORATION, Midland, MI (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/537,630

(22) PCT Filed: Nov. 13, 2015

(86) PCT No.: PCT/US2015/060593
§ 371 (c)(1),
(2) Date: Jun. 19, 2017

(87) PCT Pub. No.: WO2016/099727
PCT Pub. Date: Jun. 23, 2016

(65) Prior Publication Data
US 2018/0036724 A1 Feb. 8, 2018

Related U.S. Application Data

(60) Provisional application No. 62/094,316, filed on Dec. 19, 2014.

(51) Int. Cl.
| | |
|---|---|
| *C07F 15/06* | (2006.01) |
| *C09K 3/00* | (2006.01) |
| *B01J 31/02* | (2006.01) |
| *B01J 31/16* | (2006.01) |
| *C07F 15/02* | (2006.01) |
| *C07F 9/58* | (2006.01) |
| *B01J 31/18* | (2006.01) |
| *C07F 7/08* | (2006.01) |
| *C07F 7/18* | (2006.01) |

(52) U.S. Cl.
CPC ......... *B01J 31/1608* (2013.01); *B01J 31/189* (2013.01); *C07F 7/0829* (2013.01); *C07F 7/1876* (2013.01); *C07F 9/582* (2013.01); *C07F 15/02* (2013.01); *C07F 15/025* (2013.01); *C07F 15/06* (2013.01); *C07F 15/065* (2013.01); *B01J 2231/323* (2013.01); *B01J 2531/842* (2013.01); *B01J 2531/845* (2013.01)

(58) Field of Classification Search
CPC ............ C07F 15/06; B01J 31/02; C09K 3/00
USPC .................. 546/2; 502/171; 252/182.12
See application file for complete search history.

(56) References Cited

U.S. PATENT DOCUMENTS

| | | | |
|---|---|---|---|
| 2,676,182 | A | 4/1954 | Daudt et al. |
| 3,159,601 | A | 12/1964 | Ashby |
| 3,296,291 | A | 1/1967 | Chalk et al. |
| 3,330,972 | A | 7/1967 | Malan |
| 3,419,593 | A | 12/1968 | Willing |
| 3,516,946 | A | 6/1970 | Modic |
| 3,814,730 | A | 6/1974 | Karstedt |
| 3,989,668 | A | 11/1976 | Lee et al. |
| 4,370,358 | A | 1/1983 | Hayes et al. |
| 4,584,355 | A | 4/1986 | Blizzard et al. |

(Continued)

FOREIGN PATENT DOCUMENTS

| | | |
|---|---|---|
| CN | 104513146 A | 4/2015 |
| EP | 0 347 895 B1 | 12/1989 |

(Continued)

OTHER PUBLICATIONS

International Search Report for Application No. WO PCT/US2015/060593 dated Jun. 23, 2016, 6 pages.
English language abstract and machine-assisted English translation for CN 104513146 extracted from espacenet.com database on Jun. 28, 2017, 17 pages.
Balaraman, Ekambaram et al., "Direct Hydrogenation of Amides to Alcohols and Amines Under Mild Conditions", J. Am. Chem. Soc., vol. 132, 2010, pp. 16756-16758.
Chang, Mee et al., "Dimensionality Control of Vapochromic Hydrogen-Bonded Porton-Transfer Assemblies Composted of a Bis(hydrazone)iron(II) Complex", Inorg. Chem., vol. 50, 2011, pp. 8308-8317.
Connelly, Neil G. et al. "Chemical Redox Agents for Organometallic Chemistry", Chem. Rev., vol. 96, 1996, pp. 877-910.

(Continued)

*Primary Examiner* — Charanjit Aulakh
(74) *Attorney, Agent, or Firm* — Howard & Howard Attorneys PLLC

(57) ABSTRACT

A ligand component is formed according to formula (1): $R^1{}_2P\text{—}X\text{—}N\!\!=\!\!C(R^2)\text{—}Y$, wherein $R^1$ is Ph or Cyc or a $C_1\text{-}C_{20}$ substituted or unsubstituted ailkyl group; each Ph is a substituted or unsubstituted phenyl group; each Cyc is a substituted or unsubstituted cycloalkyl group; X is an unsubstituted arylene or a $C_2\text{-}C_3$ substituted or unsubstituted alkylene; $R^2$ is H, methyl or Ph; and Y N is pyridyl, 6-phenylpyridyl or 6-methylpyridyl; with the proviso that when X is a $C_2$ substituted or unsubstituted alkylene and Y is pyridyl, $R^2$ is methyl or Ph. A reaction product including the ligand component and a metal precursor is prepared by combining the ligand component with the metal precursor. An activated reaction product is formed by activating the reaction product as a hydrosilylation catalyst.

23 Claims, No Drawings

(56) References Cited

U.S. PATENT DOCUMENTS

| | | | |
|---|---|---|---|
| 4,585,836 | A | 4/1986 | Homan et al. |
| 4,591,622 | A | 5/1986 | Blizzard et al. |
| 4,707,531 | A | 11/1987 | Shirahata |
| 4,766,176 | A | 8/1988 | Lee et al. |
| 4,784,879 | A | 11/1988 | Lee et al. |
| 5,017,654 | A | 5/1991 | Togashi et al. |
| 5,036,117 | A | 7/1991 | Chung et al. |
| 5,175,325 | A | 12/1992 | Brown et al. |
| 5,310,843 | A | 5/1994 | Morita |
| 8,236,915 | B2 | 8/2012 | Delis et al. |
| 2007/0021607 | A1 | 1/2007 | Small et al. |
| 2013/0228100 | A1 | 9/2013 | Kleyer et al. |
| 2014/0231703 | A1 | 8/2014 | Brandstadt et al. |

FOREIGN PATENT DOCUMENTS

| | | |
|---|---|---|
| WO | WO 03/093349 A1 | 11/2003 |
| WO | WO 03/093369 A1 | 11/2003 |
| WO | WO 2013/023307 A1 | 2/2013 |

OTHER PUBLICATIONS

Dalili, S. et al., "Aziridine-Derived Iminophosphone Ligands in Palladium-Catalyzed Allylic Sustitution", Journal of Organometallic Chemistry, 2004, vol. 689, No. 22, pp. 3604-3611.

Del Zotto, Alessandro et al., "[MCl(ligand)]+ Complexes (M=Ni, Pd, Pt) with a P,N,N Terdantate Ligand-Solid State and Solution Structures and Catalytic Activity of the PdII Derivative in the Heck Reaction", Eur. J. Inorg. Chem., 2005, pp. 4707-4714.

Doherty, Simon et al., "Iminophosphines: Synthesis, Formation of 2,3-Dihydro-1H-benzo[1,3]Azaphosphol-3-ium Salts and N-(Pyridin-2-yl)-2-Diphenylphosphinoylaniline, Coordination Chemistry and Applications in Platinum Group Catalyzed Suzuki Coupling Reactions and Hydrosilylations", Journal of Organometallic Chemistry, vol. 650, 2002, pp. 231-248.

Dubois, Thomas D. et al., "Four-and-Five-Coordinate Nickel(II) Complexes of 2,3-Butanedionebis(2-Diphenylphosphinoethylimine)", Inorganic Chemistry, vol. 11, No. 4, 1972, pp. 718-722.

Ebisu, Y., et al., "Enantioselective Copper-Catalyzed 1,4-Addition of Dialkylzincs to Enones Using a Novel N,N,P—Cu(II) Complex, "Tetrahedron: Asymmetry, 2012, vol. 23, No. 13, pp. 959-964.

Gilbert-Wilson, R. et al., "Phosphine-Imonopyrides as Platforms for Catalytic Hydrofunctionalization of Alkenes", Inorganic Chemistry, (Epub.), May 15, 2015, vol. 54, No. 11, pp. 5596-5603.

Han, F. et al., "Highly Enantioselective Copper-Catalyzed Propargylic Substitution of Propargylic Acetates with 1,3-Dicarbonyl Compounds", Organic Letters, 2013, vol. 16, pp. 588-591.

Hou, Junxian et al., "Synthesis and Characterization of Tridentate Nickel Compleses Bearing P N P Ligands and Their Catalytic Property in Ethylene Oligomerization", Organometallics, vol. 25, 2006, pp. 236-244.

Li, Q. et al., "Tridentate P,N,N-Ligand Promoted Copper-Catalyzed [3+2] Cycloaddition of Propargylic Esters with b-Enamino Esters: Synthesis of Highly Functionalized Pyrroles", RSC Advances, [Epub.], Oct. 5, 2015, vol. 5, No. 104, pp. 85979-85883.

Morimoto, T. et al., "Enantioselective Copper-Catalyzed Conjugate Addition of Diethylzinc to Enones Using New Chiral P,N Ligands Composed of (S)-2-alky 1-2-aminoethylphosphines and a-substitued pyridines", Tetrahedron, 2000, vol. 41, No. 51, pp. 10025-10029.

Mukhopadhyay, Tufan K., "A Highly Active Manganese Precatalyst for the Hydrosilylation of Ketones and Esters", J. Am. Chem. Soc., vol. 136, 2014, pp. 882-885.

Peng, Dongjie et al., "Phosphinite-Iminopyridine Iron Catalysts for Chemoselective Alkene Hydrosilylation", J. Am. Chem. Soc., vol. 135, 2013, pp. 19154-19166.

Porter, Tyler M. et al., "Importance of Co-Donor Field Strength in the Preparation of Tetradentate a-Diimine Nickel Hydrosilylation Catalysts", Dalton Trans., vol. 42, 2013, pp. 14689-14692.

Schmiege, Benjamin M. et al., "Alternatives to Pyridinediimine Ligands: Syntheses and Structures of Metal Complexes Supported by Donor-Modified a-diimine Ligands", Dalton Trans., 2007, pp. 2547-2562.

Spasyuk, Denis et al., "Acceptorless Dehydrogenative Coupling of Ethanol and Hydrogenation of Esters and Imines," Organometallics, vol. 31, 2012, pp. 5239-5242.

Zhu, F. et al., "Enantioselective Synthesis of Highly Functionaled Dihydrofurans Through Copper-Catalyzed Asymmetric Formal [3+2] Cycloaddition of B-Ketoesters with Propargylic Esters", Agnew. Chem. Int. ed., (Epub.], Aug. 1, 2014, vol. 54, No. 38, pp. 10223-10227.

LIGAND COMPONENTS, ASSOCIATED REACTION PRODUCTS, ACTIVATED REACTION PRODUCTS, HYDROSILYLATION CATALYSTS AND HYDROSILYLATION CURABLE COMPOSITIONS INCLUDING THE LIGAND COMPONENTS, AND ASSOCIATED METHODS FOR PREPARING SAME

RELATED APPLICATIONS

The subject application is the National Stage of International Patent Application No. PCT/US2015/060593, filed Nov. 13, 2015, which claims priority to U.S. Provisional Patent Application No. 62/094,316, filed on Dec. 19, 2014.

FIELD OF THE INVENTION

The present invention generally relates to ligand components, activated reaction products formed from these ligand components, and the subsequent use of these activated reaction products as hydrosilylation catalysts in hydrosilylation curable compositions. The present invention also generally relates to the associated methods for preparing these activated reaction products and hydrosilylation curable compositions.

BACKGROUND OF THE INVENTION

Catalysts for catalyzing hydrosilylation reaction are known in the art and are commercially available. Such conventional hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

These hydrosilylation catalysts suffer from the drawback of being extremely costly. Some of the metals in these hydrosilylation catalysts may also be difficult to obtain, and some of these hydrosilylation catalysts may be difficult to prepare. There is a need in industry to replace the conventional hydrosilylation catalysts described above with a less expensive and/or more readily available alternatives.

SUMMARY OF THE INVENTION

A ligand component, and methods for preparation of the ligand component, is disclosed. The ligand component is according to formula (1): $R^1_2P$—X—N=$C(R^2)$—Y, wherein $R^1$ is Ph or Cyc or a $C_1$-$C_{20}$ substituted or unsubstituted alkyl group; each Ph is a substituted or unsubstituted phenyl group; each Cyc is a substituted or unsubstituted cycloalkyl group; X is an unsubstituted arylene or a $C_2$-$C_3$ substituted or unsubstituted alkylene; $R^2$ is H, methyl or Ph; and Y is pyridyl or 6-phenylpyridyl or 6-methylpyridyl; with the proviso that when X is a $C_2$ substituted or unsubstituted alkylene and Y is pyridyl, $R^2$ is methyl or Ph.

In addition, a reaction product of components comprising a metal precursor and the ligand component, and methods for preparation of the reaction product, is disclosed. The metal precursor is according to formula (2): $[M-A_x]_n$, wherein M is a metal selected from iron, cobalt, manganese, nickel, and ruthenium; wherein each A is independently a displaceable substituent; wherein subscript x is an integer with a value ranging from 1 to a maximum valence number of M; and wherein n is 1 or 2.

Still further, an activated reaction product comprises the reaction product combined with an ionic activator or a reducing agent. The activated reaction product is useful as a hydrosilylation catalyst and provides advantages over previous hydrosilylation catalysts as described above in terms of material costs and ease of preparation. In this regard, the present invention also discloses compositions that utilize the activated reaction product. Thus, the present invention discloses compositions comprising the activated reaction product (A); (B) a compound having an average, per molecule, of one or more aliphatically unsaturated organic groups; and optionally (C) an Si—H functional compound having an average, per molecule, of at least one silicon-bonded hydrogen atom, wherein component (C) is present when component (B) does not a silicon-bonded hydrogen atom.

DETAILED DESCRIPTION OF THE INVENTION

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, or an aralkyl group includes the member alkyl individually; the subgroup alkyl and aryl; and any other individual member and subgroup subsumed therein.

"Alkyl" means an acyclic, branched or unbranched, saturated monovalent hydrocarbon group. Alkyl is exemplified by, but not limited to, methyl, ethyl, propyl (e.g., isopropyl and/or n-propyl), butyl (e.g., isobutyl, n-butyl, tert-butyl, and/or sec-butyl), pentyl (e.g., isopentyl, neopentyl, and/or tert-pentyl), hexyl, heptyl, octyl, nonyl, and decyl, as well as branched saturated monovalent hydrocarbon groups of 6 or more carbon atoms.

"Alkylene" means a bivalent saturated aliphatic group as derived from an alkene by opening of the double bond or from an alkane by removal of two hydrogen atoms from different carbon atoms. The alkylene may be substituted or unsubstituted.

"Aryl" means a cyclic, fully unsaturated, hydrocarbon group. Aryl is exemplified by, but not limited to, cyclopentadienyl, phenyl, anthracenyl, and naphthyl. Monocyclic aryl groups may have 5 to 9 carbon atoms, alternatively 6 to 7 carbon atoms, and alternatively 5 to 6 carbon atoms. Polycyclic aryl groups may have 10 to 17 carbon atoms, alternatively 10 to 14 carbon atoms, and alternatively 12 to 14 carbon atoms.

"Arylene" means a bivalent aryl group derived from an aromatic hydrocarbon by removal of a hydrogen atom from each of two carbon atoms of the nucleus. The arylene group has two free valences, each of which is at a carbon atom, which may be the same or different.

"Aralkyl" means an alkyl group having a pendant and/or terminal aryl group or an aryl group having a pendant alkyl group. Exemplary aralkyl groups include tolyl, xylyl, benzyl, phenylethyl, phenyl propyl, and phenyl butyl. The pendent or terminal aryl group or alkyl groups may be substituted or unsubstituted.

"Carbocycle" and "carbocyclic" each mean a hydrocarbon ring. Carbocycles may be monocyclic or alternatively may be fused, bridged, or spiro polycyclic rings. Monocyclic carbocycles may have 3 to 9 carbon atoms, alternatively 4 to 7 carbon atoms, and alternatively 5 to 6 carbon atoms. Polycyclic carbocycles may have 7 to 17 carbon atoms, alternatively 7 to 14 carbon atoms, and alternatively 9 to 10 carbon atoms. Carbocycles may be saturated or partially unsaturated.

"Cycloalkyl" means saturated carbocycle. Monocyclic cycloalkyl groups are exemplified by cyclobutyl, cyclopentyl, and cyclohexyl. Cycloalkyl groups may be substituted or unsubstituted.

"Halogenated hydrocarbon" means a hydrocarbon where one or more hydrogen atoms bonded to a carbon atom have been formally replaced with a halogen atom. Halogenated hydrocarbon groups include haloalkyl groups, halogenated carbocyclic groups, and haloalkenyl groups. Haloalkyl groups include fluorinated alkyl groups such as trifluoromethyl ($CF_3$), fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; and chlorinated alkyl groups such as chloromethyl and 3-chloropropyl. Halogenated carbocyclic groups include fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl, 2,3-dichlorocyclopentyl. Haloalkenyl groups include allyl chloride.

"Heteroatom" means any of the Group 13-17 elements of the IUPAC Periodic Table of the Elements at http://www.iupac.org/fileadmin/user_upload/news/IUPAC_Periodic_Table-1Jun12.pdf, except carbon. "Heteroatom" include, for example, N, O, P, S, Br, Cl, F, and I.

"Heteroatom containing group" means an organic group comprised of a carbon atom and that also includes at least one heteroatom. Heteroatom containing groups may include, for example, one or more of acyl, amide, amine, carboxyl, cyano, epoxy, hydrocarbonoxy, imino, ketone, ketoxime, mercapto, oxime, and/or thiol. For example, when the heteroatom containing group contains one or more halogen atoms, then the heteroatom containing group may be a halogenated hydrocarbon group as defined above. Alternatively, when the heteroatom is oxygen, then the heteroatom containing group may be a hydrocarbonoxy group such as an alkoxy group or an alkylalkoxy group.

"Inorganic heteroatom containing group" means group comprised of at least 1 heteroatom and at least 1 of hydrogen or a different heteroatoms. Heteroatom containing groups may include, for example, one or more of amine, hydroxyl, imino, nitro, oxo, sulfonyl, and/or thiol.

"Heteroalkyl" group means an acyclic, branched or unbranched, saturated monovalent hydrocarbon group that also includes at least one heteroatom. "Heteroalkyl" includes haloalkyl groups and alkyl groups in which at least one carbon atom has been replaced with a heteroatom such as N, O, P, or S, e.g., when the heteroatom is O, the heteroalkyl group may be an alkoxy group.

"Heterocycle" and "heterocyclic" each mean a ring group comprised of carbon atoms and one or more heteroatoms in the ring. The heteroatom in the heterocycle may be N, O, P, S, or a combination thereof. Heterocycles may be monocyclic or alternatively may be fused, bridged, or spiro polycyclic rings. Monocyclic heterocycles may have 3 to 9 member atoms in the ring, alternatively 4 to 7 member atoms, and alternatively 5 to 6 member atoms. Polycyclic heterocycles may have 7 to 17 member atoms, alternatively 7 to 14 member atoms, and alternatively 9 to 10 member atoms. Heterocycles may be saturated or partially unsaturated.

"Heteroaromatic" means a fully unsaturated ring containing group comprised of carbon atoms and one or more heteroatoms in the ring. Monocyclic heteroaromatic groups may have 5 to 9 member atoms, alternatively 6 to 7 member atoms, and alternatively 5 to 6 member atoms. Polycyclic heteroaromatic groups may have 10 to 17 member atoms, alternatively 10 to 14 member atoms, and alternatively 12 to 14 member atoms. Heteroaromatic includes heteroaryl groups such as pyridyl. Heteroaromatic includes heteroaralkyl, i.e., an alkyl group having a pendant and/or terminal heteroaryl group or a heteroaryl group having a pendant alkyl group. Exemplary heteroaralkyl groups include 6-methylpyridyl and dimethylpyridyl.

Abbreviations used herein are defined as follows. The abbreviation "cP" means centiPoise, and "cSt" means centiStokes. "DP" means the degree of polymerization. "FTIR" means Fourier transform infrared spectroscopy. "GC" means gas chromatography. "GPC" means gel permeation chromatography. "$M_n$" means number average molecular weight. $M_n$ may be measured using GPC. "$M_w$" means weight average molecular weight. "NMR" means nuclear magnetic resonance. "Pa·s" means Pascal seconds, and "ppm" means parts per million. "COD" means cyclooctadienyl. "Et" means ethyl. "Me" means methyl. "Ph" means phenyl (i.e., substituted or unsubstituted phenyl groups). "Pr" means propyl and includes various structures such as iPr and nPr. "iPr" or "iPr" means isopropyl. "nPr" means normal propyl. "Bu" means butyl and includes various structures including nBu, sec-butyl, tBu, and iBu. "iBu" or "iBu" means isobutyl. "nBu" means normal butyl. "tBu" means tert-butyl. "AcAc" means acetyl acetonate. "2-EHA" means 2-ethylhexanoate. "OAc" means acetate. "Hex" means hexenyl. "THF" means tetrahydrofuran. "Vi" means vinyl.

"M-unit" means a siloxane unit having formula $R_3SiO_{1/2}$, where each R independently represents a monovalent atom or organic group. "D-unit" means a siloxane unit having formula $R_2SiO_{2/2}$, where each R independently represents a monovalent atom or group. "T-unit" means a siloxane unit having formula $RSiO_{3/2}$, where each R independently represents a monovalent atom or group. "Q-unit" means a siloxane unit having formula $SiO_{4/2}$.

"Non-functional" means that the component does not have either an aliphatically unsaturated substituent or a silicon bonded hydrogen atom that could participate in a hydrosilylation reaction.

"Free of" means that the composition contains a non-detectable amount of the component, or the composition contains an amount of the component insufficient to change the GC measurement measured as described in the Examples section, as compared to the same composition with the component omitted. For example, the composition described herein may be free of platinum catalysts. "Free of platinum catalysts" means that the composition contains a non-detectable amount of a platinum catalyst capable of catalyzing a hydrosilylation reaction with the unsaturated groups on other components in the composition, or the composition contains an amount of a platinum catalyst insufficient to change the GC measurement measured as described in the Examples section, as compared to the same composition with the platinum catalyst omitted. The composition may be free of conventional metal catalysts. "Free of conventional metal catalysts" means that the composition contains a non-detectable amount of a the metal selected from Pt, Rh, Pd, and Os, or the compound of such a metal capable of catalyzing a hydrosilylation reaction with the unsaturated groups on other components in the composition, or the composition contains an amount of the conventional metal catalyst insufficient to change the GC measurement measured as described in the Examples section, as compared to the same composition with the conventional metal catalyst omitted. Alternatively, the composition described herein may be free of hydrosilylation reaction catalysts (i.e., free of any component capable of catalyzing a hydrosilylation reaction of the aliphatically unsaturated groups on component (B), described below, other than component (A) described herein).

As noted above, the present invention discloses ligand components, and reaction products including the ligand components. The present invention also discloses, in certain embodiments, an activated reaction product including the reaction product combined with an ionic activator. In addition, the present invention relates the activated reaction products that are useful as hydrosilylation catalysts, and compositions that utilize the activated reaction products, as will be described in further detail below.

The ligand component (sometimes also referred to as PNN), in certain embodiments of the present invention, is according to the general formula (1): $R^1{}_2P-X-N=C(R^2)-Y$, wherein $R^1$ is Ph or Cyc or $C_1$-$C_{20}$ substituted or unsubstituted alkyl group; each Ph is a substituted or unsubstituted phenyl group: each Cyc is a substituted or unsubstituted cycloalkyl group; X is an unsubstituted arylene or a $C_2$-$C_3$ substituted or unsubstituted alkylene; $R^2$ is H, methyl or Ph; and Y is pyridyl or 6-phenylpyridyl or 6-methylpyridyl; with the proviso that when X is a $C_2$ substituted or unsubstituted alkylene and Y is pyridyl, $R^2$ is methyl or Ph (i.e., $R^2$ cannot be H when X is a $C_2$ substituted or unsubstituted alkylene and Y is pyridyl).

In certain embodiments, $R^1$ is a $C_1$-$C_{10}$ substituted or unsubstituted alkyl group, such as a $C_2$-$C_5$ substituted or unsubstituted alkyl group, such as a $C_3$ or $C_4$ substituted or unsubstituted alkyl group.

In more specific embodiments, the ligand component of formula (1) is further defined according to any one or more of formulas (1A)-(1I) below:

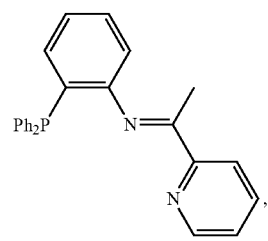
(1A)

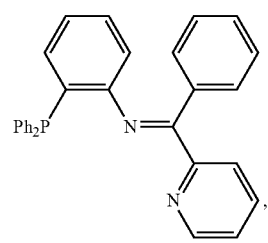
(1B)

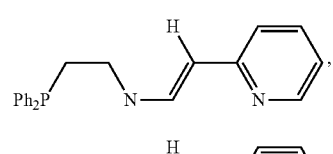
(1C)

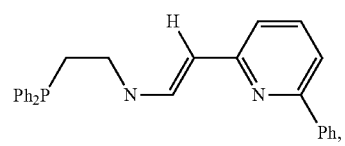
(1D)

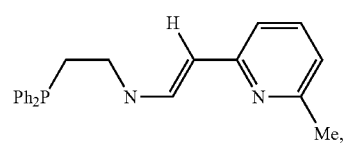
(1E)

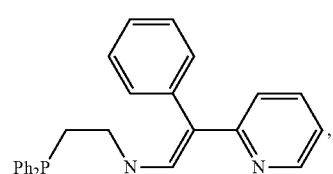
(1F)

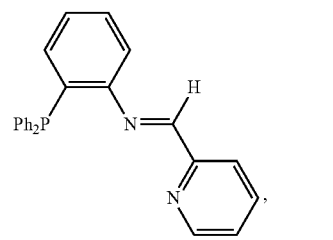
(1G)

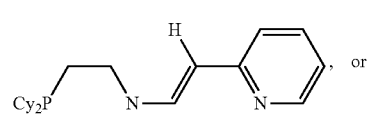
(1H)

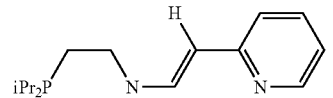
(1I)

wherein each Ph is an unsubstituted phenyl group, wherein Cy is an unsubstituted cyclohexyl group and iPr is an isopropyl group.

Formulas (1A)-(1I) above may alternatively be referred to herein by their respective PNN designation, the designations of which are described at the beginning of the Examples Section below. More specifically, Formula (1A) above may alternatively be referred to as $P^{Ar}N^{Me}N$; Formula (1B) above may alternatively be referred to as $P^{Ar}N^{Ph}N$; Formula (1C) above may alternatively be referred to as $P^{Pr}N^{H}N^{H}$; Formula (1D) above may alternatively be referred to as $P^{Pr}N^{H}N^{Ph}$; Formula (1E) above may alternatively be referred to as $P^{Pr}N^{H}N^{Me}$; Formula (1F) above may alternatively be referred to as $P^{Pr}N^{Ph}N$; Formula (1G) above may alternatively be referred to as $P^{Ar}N^{H}N$; Formula (1H) above may alternatively be referred to as $CyP^{Pr}N^{H}N$; and Formula (1I) above may alternatively be referred to as $PrP^{Pr}N^{H}N$.

The ligand component, in accordance with the present invention, may be produced by treating a phosphino-group containing component according to the formula (3) with a pyridine-containing component according to formula (4):

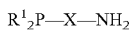

$$R^1{}_2P-X-NH_2 \quad (3),$$

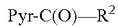

$$Pyr-C(O)-R^2 \quad (4),$$

In formulae (3) and (4), Pyr is a pyridyl group, while X, $R^1$ and $R^2$ are as defined above with respect to general formula (1).

In more specific embodiments, the phosphino-group containing component according to the formula (3) is further defined according to any one or more of formulas (3A)-(3D) below:

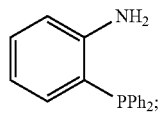

(3A)

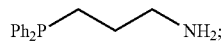

(3B)

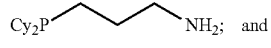

(3C)

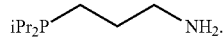

(3D)

In formulas (3A)-(3D), Ph is an unsubstituted phenyl group, Cy is an unsubstituted cyclohexyl group and iPr is an isopropyl group.

In more specific embodiments, the pyridine-containing component according to formula (4) is further defined according to any one or more of formulas (4A)-(4E) below:

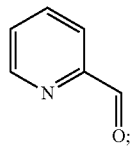

(4A)

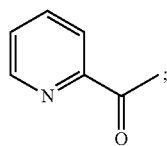

(4B)

-continued

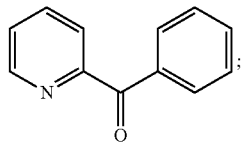

(4C)

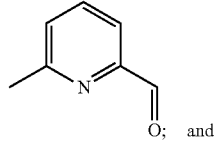

(4D)

and

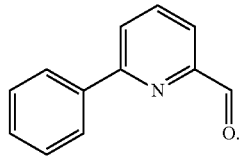

(4E)

The present invention is also directed to reaction products that include the ligand component, in accordance with any embodiment above, and a metal precursor. The present invention is also directed to the associated methods for preparing these reaction products.

The metal precursor, or M precursor, may be a metal compound having general formula (2): $[M-A_x]_n$, where M is a metal atom selected from the group consisting of iron (Fe), cobalt (Co), manganese (Mn), nickel (Ni), zinc (Zn) and ruthenium (Ru):

each A is independently a displaceable substituent;

subscript x is an integer with a value ranging from 1 to the maximum valence number of the metal atom selected for M; and n is 1 or 2.

The M precursor may have any one of formulas (a), (b), (c), (d), or (e). To this end, formula (a) is $[Fe-A_x]$, formula (b) is $[Co-A_x]$, formula (c) is $[Mn-A_x]$, formula (d) is $[Ni-A_x]$, and formula (e) is $[Ru-A_x]_2$. Alternatively, M may be any one of Fe, Co. Mn, Ni and Ru. Without wishing to be bound by theory, it is thought that one or more instances of A can be displaced from M by the ligand component to form the reaction product. Without wishing to be bound by theory, it is thought that one or more instances of group A are displaced by a complexation reaction between the M precursor and the ligand component to form the reaction product. When subscript x is greater than 1, then each instance of A in the general formula for the M precursor may be the same or different. Examples for A include halogen atoms and monovalent organic groups. The monovalent organic group may be a monovalent hydrocarbon group or a monovalent heteroatom containing group. The monovalent heteroatom containing group is exemplified by amino groups, halogenated hydrocarbon groups, silazane groups, carboxylate groups, carboxylic ester groups, carbonyl groups, hydrocarbonoxy groups, suffonate ester groups, suffonylimide groups, acetate groups, and cyano groups.

Examples of halogen atoms for A in the general formula (2) for the M precursor include Br, Cl, or I. Examples of monovalent halogenated hydrocarbon groups for A in general formula (2) include haloalkyl groups, e.g., fluorinated alkyl groups such as $CF_3$, fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; and chlorinated alkyl groups such as chloromethyl and 3-chloropropyl; halogenated carbocyclic groups such as fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl, 2,3-dichlorocyclopentyl; and haloalkenyl groups such as allyl chloride.

Examples of monovalent hydrocarbon groups for A in the general formula (2) for the M precursor include, but are not limited to, alkyl, alkenyl, carbocyclic, aryl, and aralkyl. Alkyl groups are exemplified by Me, Et, Pr, Bu, pentyl, hexyl, heptyl, ethylhexyl, octyl, decyl, dodecyl, undecyl, and octadecyl. Alkenyl groups are exemplified by Vi, allyl, propenyl, and Hex. Carbocyclic groups are exemplified by saturated carbocyclic groups, e.g., cycloalkyl such as cyclopentyl and cyclohexyl, or unsaturated carbocyclic groups, e.g., cycloalkenyl such as cyclopentadienyl, cyclohexenyl, or cyclooctadienyl. Aryl groups are exemplified by Ph, tolyl, xylyl, mesityl, and naphthyl. Aralkyl groups are exemplified by benzyl and 2-phenylethyl.

Examples of amino groups for A in the general formula (2) for the M precursor have formula —NA'$_2$, where each A' is independently a hydrogen atom or a monovalent hydrocarbon group. Exemplary monovalent hydrocarbon groups for A' include, but are not limited to, alkyl such as Me, Et, Pr, Bu, pentyl, hexyl, heptyl, ethylhexyl, octyl, decyl, dodecyl, undecyl, and octadecyl; alkenyl such as vinyl, allyl, propenyl, and Hex; carbocyclic groups exemplified by saturated carbocyclic groups, e.g., cycloalkyl such as cyclopentyl and cyclohexyl, or unsaturated carbocyclic groups such as cyclopentadienyl or cyclooctadienyl; aryl such as Ph, tolyl, xylyl, mesityl, and naphthyl; and aralkyl such as benzyl or 2-phenylethyl. Alternatively, each A' may be a hydrogen atom or an alkyl group of 1 to 4 carbon atoms, such as Me or Et.

Alternatively, each A in the general formula (2) for the M precursor may be a silazane group. Alternatively, each A in the general formula for the M precursor may be a carboxylic ester group. Examples of suitable carboxylic ester groups for A include, but are not limited to OAc, ethylhexanoate (such as 2-EHA), neodecanoate, octanoate, and stearate.

Examples of monovalent hydrocarbonoxy groups for A in the general formula (2) for the M precursor may have formula —O-A", where A" is a monovalent hydrocarbon group. Examples of monovalent hydrocarbon groups for A" include, but are not limited to, alkyl such as Me, Et, Pr, Bu, pentyl, hexyl, heptyl, ethylhexyl, octyl, decyl, dodecyl, undecyl, and octadecyl; alkenyl such as Vi, allyl, propenyl, and Hex; cycloalkyl such as cyclopentyl and cyclohexyl; aryl such as Ph, tolyl, xylyl, and naphthyl; aralkyl such as benzyl or 2-phenylethyl. Alternatively, each A" may be an alkyl group, such as Me, Et, nPr, iPr, nBu, iBu, or tBu. Alternatively, each A" may be an alkyl group, and alternatively each A" may be Et, Pr such as iPr or nPr, or Bu.

Alternatively, each A in the general formula (2) for the M precursor may be an alkyl group, such as Me, Et, nPr, iPr, nBu, iBu, or tBu. Alternatively, each A may be independently selected from the group consisting of Et, benzyl, mesityl, Ph, NEt$_2$, NMe$_2$, cyclooctadiene, ethoxide, iPr, Bu, 2-EHA, ethoxy, propoxy, methoxy, and carbonyl.

Alternatively, the M precursor may be a commercially or synthetically available compound, such as those shown below in Table 1.

| Name | Vendor/Source |
|---|---|
| Cobalt(II) iodide | Strem |
| Cobalt(II) bis(trimethylsilyl amide) | Dow Corning |
| Iron(II) bromide | Sigma Aldrich |
| Iron(II) bis(trimethylsilyl amide) | Dow Corning |
| Nickel(II) bromide dimethoxyethane | Strem |
| Nickel(II) bis(trimethylsilyl amide) | Dow Corning |
| Bis(2-methylallyl)(1,5-cyclo-octadiene) ruthenium(II) | Strem |
| Dichloro(benzene) ruthenium(II) dimer | Strem |

In Table 1, "Dow Corning" refers to Dow Corning Corporation of Midland, Michigan, U.S.A., "Sigma-Aldrich" refers to Sigma-Aldrich, Inc. of St. Louis, Missouri, U.S.A., and "Strem" refers to Strem Chemicals Inc. of Newburyport, Massachusetts, U.S.A.

In more specific embodiments, the metal precursor may be iron (ii) bromide, cobalt (II) chloride, cobalt (I) chloride, cobalt (I) Me, and any combination thereof.

In certain embodiments, the reaction product (of formula (2) with formula (1)) is further defined according to any one or more of formulas (2A)-(2H) below:

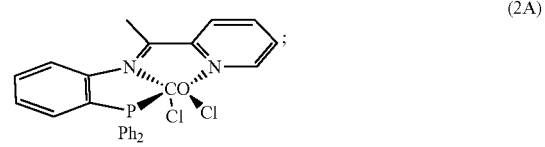
(2A)

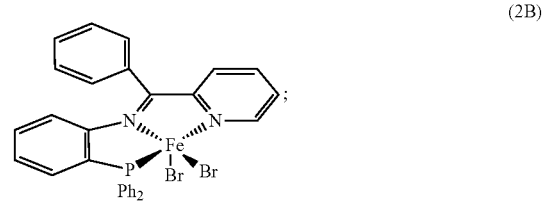
(2B)

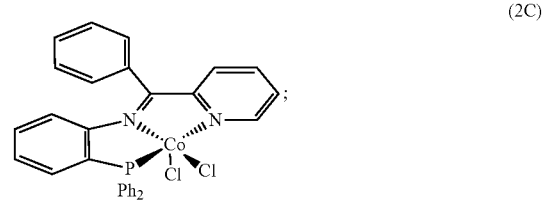
(2C)

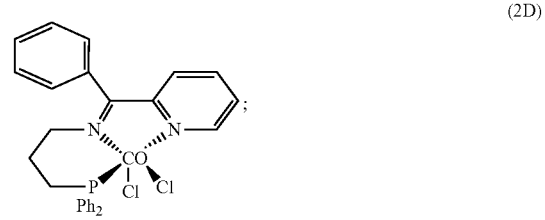
(2D)

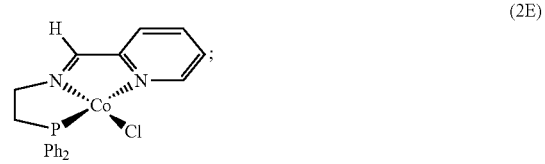
(2E)

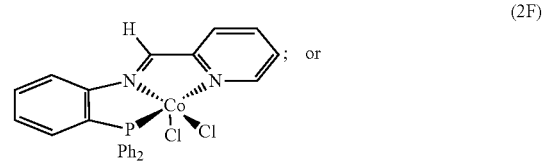
(2F)

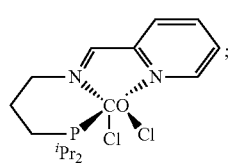

(2G)

wherein each Ph is an unsubstituted phenyl group.

Similar to Formulas (1A)-(1I) above, Formulas (2A)-(2G) may alternatively be referred to by their respective metal complex—PNN designation. More specifically, Formula (2A) above may alternatively be referred to as Co($P^{Ar}N^{Me}N$)$Cl_2$; Formula (2B) above may alternatively be referred to as Fe($P^{Ar}N^{Ph}N$)$Br_2$; Formula (2C) above may alternatively be referred to as Co($P^{Ar}N^{Ph}N$)$Cl_2$; Formula (2D) above may alternatively be referred to as Co($P^{Pr}N^{Ph}N$)$Cl_2$; Formula (2E) above may alternatively be referred to as Co($P^{Et}N^{H}N$)Cl; Formula (2F) above may alternatively be referred to as Co($P^{Et}N^{H}N$)Me; Formula (2G) above may alternatively be referred to Co($P^{Ar}N^{H}N$)$Cl_2$; and Formula (2H) above may alternatively be referred to as of Co($^iPrP^{Pr}N^{H}N$)$Cl_2$.

In certain embodiments, the reaction product is activated to form an activated reaction product (i.e., a catalytically active reaction product). The activated reaction product, as will be described in further detail below, is useful as a hydrosilylation catalyst.

In certain embodiments, activating the reaction product can be performed by reducing the formal oxidation state of the metal atom in the reaction product by combining the reaction product described above with a reducing agent. Examples of reducing agents that may be combined with the reaction product include an alkali metal amalgam; hydrogen, a metal hydride such as lithium aluminum hydride ($LiAlH_4$) or sodium naphthalenide; a silyl hydride (which may be in addition to, or instead of, all or a portion of a silane crosslinker, described below); or a metal borohydride such as sodium triethylborohydride ($NaEt_3BH$), lithium triethylborohydride ($LiEt_3BH$), or sodium borohydride ($NaBH_4$). Suitable reducing agents include those described in Chem. Rev. 1996, 96, 877-910.

Alternatively, the reaction product described above can be activated by a process comprising combing the reaction product described above with an ionic activator. Examples of ionic activators for use in the reaction product include carboranes, such as $Li^+[CB_{11}H_6Br_6]^-$, $Li^+[CB_9H_5Br_5]^-$, $Li^+[CB_{11}H_{10}Br_2]^-$, and $Li^+[CB_9H_8Br_2]^-$, $NH_4^+[CB_{11}H_6Br_6]^-$, $NH_4^+[CB_9H_5Br_5]^+$, $NH_4^+[CB_{11}H_{10}Br_2]^-$, $NH_4^+[CB_9H_8Br_2]^-$, $Na^+[CB_{11}H_6Br_6]^-$, $Na^+[CB_9H_5Br_5]^-$, $Na^+[CB_{11}H_{10}Br_2]^-$, and $Na^+[CB_9H_8Br_2]^-$; or metal borates such as lithium tetrakis(pentafluorophenyl)borate (LiBArF), lithium tetrakis(3,5-trifluoromethyl)phenylborate, sodium tetrakis(3,5-trifluoromethyl)phenylborate, or a mixture thereof.

Additional suitable ionic activators, in addition to those described above, may also include ionic activators that include silicon atoms. A non-limiting list of exemplary silicon-containing ionic activators include $NaN(SiMe_3)_2$, $LiN(SiMe_3)_2$, $LiC(SiMe_3)_3$, and $LiCH_2SiMe_3$.

Still further examples of other suitable ionic activators include, but are not limited to, $CH_3Li$, BuLi, PhLi, MeMgCl, MeMgBr, and (allyl)MgBr.

One exemplary activated product, which is formed by reacting the ligand component $P^{Et}N^HN$ with $CoCl_2$, followed by the reaction with a MeLi activator, is illustrated below as Formula (2H), wherein Ph is an unsubstituted phenyl group:

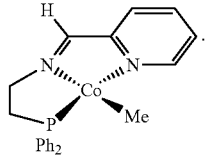

(2H)

The present invention is also directed to compositions that include at least one component capable of undergoing a hydrosilylation reaction.

In certain embodiments, the composition, which has at least one component capable of reacting by hydrosilylation reaction (composition), comprises:
  (A) the activated reaction product; and
  (B) an aliphatically unsaturated compound having an average, per molecule, of one or more aliphatically unsaturated organic groups capable of undergoing hydrosilylation reaction.

Without wishing to be bound by theory, it is thought that the activated reaction product is characterizable as being effective for catalyzing the hydrosilylation reaction of the composition. The hydrosilylation reaction of the composition prepares a reaction product. The reaction product may have a form selected from the group consisting of a silane, a gum, a gel, a rubber, and a resin.

When component (B) does not contain a silicon bonded hydrogen atom, then the composition further comprises component (C), an SiH functional compound having an average, per molecule, of one or more silicon bonded hydrogen atoms, which is distinct from components (A) and (B).

The composition may optionally further comprise one or more additional components, which are distinct from component (A), component (B), and component (C) described above. Suitable additional components are exemplified by (D) a spacer (E) an extender, a plasticizer, or a combination thereof; (F) a filler; (G) a filler treating agent; (H) a biocide; (I) a stabilizer, (J) a flame retardant; (K) a surface modifier; (L) a chain lengthener; (M) an endblocker; (N) a flux agent; (O) an anti-aging additive; (P) a pigment; (Q) an acid acceptor (R) a rheological additive; (S) a vehicle; (T) a surfactant; (U) a corrosion inhibitor; and any combination thereof.

Component (A) may be prepared by a method comprising combining the ligand component and the M precursor, as described above. The method may optionally further comprise a step of dissolving either the M precursor, or the ligand component, or both, in a solvent before combining the M precursor and the ligand component. Suitable solvents are exemplified by those described below for component (S). Alternatively, the ligand component may be dissolved in a solvent in a container, and the solvent may thereafter be removed before adding the M precursor to the container with the ligand component. The amounts of ligand component and M precursor are selected such that the mole ratio of ligand component to M precursor (Metal:Ligand Component Ratio) may range from 10:1 to 1:10, alternatively 2:1 to 1:2, alternatively 1:1 to 1:4, and alternatively 1:1 to 1:2. Combining the M precursor and the ligand component may be performed by any convenient means, such as mixing them together in or shaking the container.

The reaction of the M precursor and ligand component may be performed by under any convenient conditions such as allowing the M precursor and ligand component prepared as described above to react at −80° C. to 200° C., alternatively room temperature (RT) of 25° C. for a period of time, by heating, or a combination thereof. Heating may be performed at, for example greater than 25° C. to 200° C., alternatively greater than 25° C. to 75° C. Heating may be performed by any convenient means, such as via a heating mantle, heating coil, or placing the container in an oven. The complexation reaction temperature depends on various factors including the including solubilities of the components and reactivities of the specific M precursor and ligand component selected and the Metal: Ligand Component Ratio, however, temperature may range from 25° C. to 200° C., alternatively 25° C. to 75° C. Complexation reaction time depends on various factors including the reaction temperature selected, however, complexation reaction time may typically range from 1 second (s) to 48 hours (h), alternatively 1 minute (min) to 30 hours (h), and alternatively 45 minutes to 15 hours. The ligand component and M precursor may be combined and heated sequentially. Alternatively, the ligand component and M precursor may be combined and heated concurrently.

The method of preparing the catalytically active reaction product of component (A) (i.e., the activated reaction product) further comprises activating the reaction product prepared as described above with the reducing agent or the ionic activator.

In certain embodiments, the activated reaction product is formed prior to being combined with component (B) (wherein component (B) contains a silicon bonded hydrogen atom) or components (B) and (C) (when component (B) does not contain a silicon bonded hydrogen atom) of the composition.

In alternative embodiments, the activated reaction product is formed in situ with component (B) (wherein component (B) contains a silicon bonded hydrogen atom) or is formed in situ with components (B) and (C) (when component (B) does not contain a silicon bonded hydrogen atom) of the composition. Stated another way, the reaction of the reaction product with the reducing agent or with the ionic activator occurs in the presence of component (B)(wherein component (B) contains a silicon bonded hydrogen atom) or in the presence of components (B) and (C)(when component (B) does not contain a silicon bonded hydrogen atom).

The method of preparing the catalytically active reaction product of component (A) may optionally further comprise adding a solvent after the reaction. Suitable solvents are exemplified by those described below for component (S). Alternatively, the method may optionally further comprise removing a reaction by-product and/or the solvent, if the solvent is present (e.g., used to facilitate combination of the M precursor and the ligand before or during the complexation reaction. By-products include, for example, H-A (where A is as defined above in the general formula for the M precursor) or any species resulting from reacting a displaceable substituent off the M precursor when the ligand reacts with the M precursor. By-products may be removed by any convenient means, such as stripping or distillation, with heating or under vacuum, and/or filtration, crystallization, or a combination thereof. The resulting isolated M-ligand complex may be used as the catalytically active reaction product of component (A).

Alternatively, the reaction by-products are not removed before using the activated reaction product as component (A). For example, the ligand component and M precursor may be reacted as described above, with or without solvent removal, and then combined with the ionic activator, and the resulting activated reaction product (comprising the activated reaction product and the reaction by-product and optionally a solvent or diluent) may be used as component (A). Without wishing to be bound by theory, it is thought that a by-product may act as a hydrosilylation reaction catalyst, or as a co-catalyst or an activator, in addition to the activated reaction product. Therefore, the reaction by-product may also catalyze the hydrosilylation reaction.

The composition may contain one single catalyst. Alternatively, the composition may comprise two or more catalysts described above as component (A), where the two or more catalysts differ in at least one property such as selection of ligand component, selection of M precursor, Metal: Ligand Component Ratio, and definitions for group A in the general formula (2) for the M precursor. The composition may be free of platinum catalysts. Alternatively, the composition may be free of conventional metal catalysts. Alternatively, the composition may be free of any M compound that would catalyze the hydrosilylation reaction of the unsaturated groups on component (B) other than the component (A). Alternatively, the composition may be free of hydrosilylation reaction catalysts other than component (A). Alternatively, the composition may be free of any component that would catalyze the hydrosilylation reaction of the unsaturated groups on component (B) other than component (A).

Component (A) is present in the composition in a catalytically effective amount. The exact amount depends on various factors including reactivity of component (A), the type and amount of component (B), and the type and amount of any additional component, if present. However, the amount of component (A) in the composition may range from 1 part per million (ppm) to 5%, alternatively 0.1% to 2%, and alternatively 1 ppm to 1%, based on total weight of all components in the composition.

Component (B) is an aliphatically unsaturated compound having an average, per molecule, of one or more aliphatically unsaturated organic groups capable of undergoing hydrosilylation reaction. Alternatively, component (B) may have an average of two or more aliphatically unsaturated organic groups per molecule. The aliphatically unsaturated organic groups may be alkenyl exemplified by, but not limited to, vinyl, allyl, propenyl, butenyl, and hexenyl. The unsaturated organic groups may be alkynyl groups exemplified by, but not limited to, ethynyl, propynyl, and butynyl.

Component (B) of the composition may be an unsaturated hydrocarbon, where the unsaturated group is capable of reacting via hydrosilylation reaction. Component (B) may be monomeric. For example, suitable aliphatically unsaturated organic compounds for component (B) include, but are not limited to alkenes such as ethylene, propene, 1-butene, 2-butene, 1-pentene, 1-hexene, 1-heptene; halogenated alkenes, such as allyl chloride; diolefins such as divinylbenzene, butadiene, 1,5-hexadiene, and 1-buten-3-yne; cycloolefins such as cyclohexene and cycloheptene; and alkynes such as acetylene, propyne, and 1-hexyne.

Oxygen-containing aliphatically unsaturated compounds can also be used for component (B), for example, where the unsaturation is ethylenic, such as vinylcyclohexyl epoxide, allyl glycidyl ether, methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid.

Heterocyclic compounds containing aliphatic unsaturation in the ring, such as dihydrofuran, and dihydropyran, are also suitable as component (B). Unsaturated compounds containing nitrogen substituents such as acrylonitrile. N-vinylpyrrolidone, alkyl cyanide, nitroethylene are also suitable as component (B).

Alternatively, component (B) of the composition comprises a polymer. Component (B) may comprise a base polymer having an average of one or more aliphatically unsaturated organic groups, capable of undergoing a hydrosilylation reaction, per molecule. Component (B) may comprise a polymer (e.g., copolymers or terpolymers) of the various compounds described above, provided there is at least one aliphatic unsaturation capable of undergoing a hydrosilylation reaction. Examples include polymers derived from olefinic monomers having 2 to 20 carbon atoms and dienes having 4 to 20 carbon atoms; polymers of monoolefin, isomonoolefin and vinyl aromatic monomers, such as monoolefins having 2 to 20 carbon groups, isomonoolefins having 4 to 20 carbon groups, and vinyl aromatic monomers including styrene, para-alkylstyrene, para-methylstyrene. Alternatively, the compounds can be poly(dienes). Most polymers derived from dienes usually contain unsaturated ethylenic units on backbone or side-chains. Representative examples include polybutadiene, polyisoprene, polybutenylene, poly(alkyl-butenylene) where alkyl includes alkyl groups having 1 to 20 carbon atoms, poly(phenylbutenylene), polypentenylene, natural rubber (a form of polyisoprene); and butyl rubber (copolymer of isobutylene and isoprene).

Alternatively, component (B) may comprise a halogenated olefin polymer having aliphatic unsaturation. Representative examples of a halogenated olefin polymer having aliphatic unsaturation include polymers resulting from the bromination of a copolymer of isomonoolefin with para-methylstyrene to introduce benzylic halogen, halogenated polybutadienes, halogenated polyisobutylene, poly(2-chloro-1,3-butadiene), polychloroprene (85% trans), poly(1-chloro-1-butenylene) (Neoprene®), and chlorosulfonated polyethylene.

Alternatively, component (B) may comprise polymers containing other compounds described above such as vinyl ether groups, acrylate groups, methyacrylate groups, and epoxy-functional groups.

Alternatively, component (B) may comprise a silane having aliphatic unsaturation. Alternatively the silane may have a general formula of: $R^{35}_{xx}SiR^{36}_{(4-xx)}$, where subscript xx is an integer from 1 to 4, alternatively 1 to 3, and alternatively 1. $R^{35}$ is an aliphatically unsaturaged organic group, and $R^{36}$ is selected from H, a halogen atom, and aa monovalent organic group.

Alternatively, component (B) may comprise a silicon containing base polymer having a linear, branched, cyclic, or resinous structure having aliphatic unsaturation. Alternatively, the base polymer may have a linear and/or branched structure. Alternatively, the base polymer may have a resinous structure. The base polymer may be a homopolymer or a copolymer. Component (B) may be one base polymer. Alternatively, component (B) may comprise two or more base polymers differing in at least one of the following properties: structure, viscosity, average molecular weight, siloxane units, and sequence. The aliphatically unsaturated organic groups in the base polymer may be located at terminal, pendant, or both terminal and pendant positions.

The remaining silicon-bonded organic groups in the base polymer for component (B) may be monovalent organic groups free of aliphatic unsaturation. Examples of monovalent hydrocarbon groups include, but are not limited to, alkyl such as Me, Et, Pr, Bu, pentyl, hexyl, heptyl, octyl, decyl, dodecyl, undecyl, and octadecyl; cycloalkyl such as cyclopentyl and cyclohexyl; aryl such as Ph, tolyl, xylyl, and naphthyl; and aralkyl such as benzyl, 1-phenylethyl and 2-phenylethyl. Examples of monovalent halogenated hydrocarbon groups include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups include, but are not limited to, hydrocarbon groups substituted with oxygen atoms such as glycidoxyalkyl, and hydrocarbon groups substituted with nitrogen atoms such as aminoalkyl and cyano-functional groups such as cyanoethyl and cyanopropyl.

Component (B) may comprise a polydiorganosiloxane of Formula (I): $R^{41}_2R^{42}SiO(R^{41}_2SiO)_a(R^{41}R^{42}SiO)_b SiR^{41}_2R^{42}$, Formula (II): $R^{41}_3SiO(R^{41}_2SiO)_c (R^{41}R^{42}SiO)_d SiR^{41}_3$, or a combination thereof. In Formulae (I) and (II), each $R^{41}$ is independently a hydrogen atom or a monovalent organic group free of aliphatic unsaturation and each $R^{42}$ is independently an aliphatically unsaturated organic group, exemplified by those described above. Subscript a may be 0 or a positive number. Alternatively, subscript a has an average value of at least 2. Alternatively subscript a may have a value ranging from 2 to 2000. Subscript b may be 0 or a positive number. Alternatively, subscript b may have an average value ranging from 0 to 2000. Subscript c may be 0 or a positive number. Alternatively, subscript c may have an average value ranging from 0 to 2000. Subscript d has an average value of at least 2. Alternatively subscript d may have an average value ranging from 2 to 2000. Suitable monovalent organic groups for $R^{41}$ are as described above for component (B). Alternatively, each $R^{41}$ is a monovalent hydrocarbon group exemplified by alkyl such as Me and aryl such as Ph. Each $R^{42}$ is independently an aliphatically unsaturated monovalent organic group as described above for component (B). Alternatively, $R^{12}$ is exemplified by alkenyl groups such as vinyl, allyl, butenyl, and hexenyl; and alkynyl groups such as ethynyl and propynyl.

Component (B) may comprise a polydiorganosiloxane such as i) dimethylvinylsiloxy-terminated polydimethylsiloxane,
ii) dimethylvinylsiloxy-terminated poly(dimethylsiloxane/methylvinylsiloxane),
iii) dimethylvinylsiloxy-terminated polymethylvinylsiloxane,
iv) trimethylsiloxy-terminated poly(dimethylsiloxane/methylvinylsiloxane),
v) trimethylsiloxy-terminated polymethylvinylsiloxane,
vi) dimethylvinylsiloxy-terminated poly(dimethylsiloxane/methylvinylsiloxane),
vii) dimethylvinylsiloxy-terminated poly(dimethylsiloxane/methylphenylsiloxane),
viii) dimethylvinylsiloxy-terminated poly(dimethylsiloxane/diphenylsiloxane), ix) phenyl,methyl,vinyl-siloxy-terminated polydimethylsiloxane,
x) dimethylhexenylsiloxy-terminated polydimethylsiloxane,
xi) dimethylhexenylsiloxy-terminated poly(dimethylsiloxane/methylhexenylsiloxane),
xii) dimethylhexenylsiloxy-terminated polymethylhexenylsiloxane,
xiii) trimethylsiloxy-terminated poly(dimethylsiloxane/methylhexenylsiloxane),
xiv) trimethylsiloxy-terminated polymethylhexenylsiloxane,
xv) dimethylhexenyl-siloxy terminated poly(dimethylsiloxane/methylhexenylsiloxane),
xvi) dimethylvinylsiloxy-terminated poly(dimethylsiloxane/methylhexenylsiloxane), and
xvii) any combination thereof.

Methods of preparing polydiorganosiloxane fluids suitable for use as component (B), such as hydrolysis and condensation of the corresponding organohalosilanes or equilibration of cyclic polydiorganosiloxanes, are well known in the art.

In addition to, or instead of, the polydiorganosiloxane described above, component (B) may further comprise a resin such as an MQ resin consisting essentially of $R^3_3SiO_{1/2}$ units and $SiO_{4/2}$ units, a TD resin consisting essentially of $R^3SiO_{3/2}$ units and $R^3_2SiO_{2/2}$ units, an MT resin consisting essentially of $R^3_3SiO_{1/2}$ units and $R^3SiO_{3/2}$ units, an MTD resin consisting essentially of $R^3_3SiO_{1/2}$ units, $R^3SiO_{3/2}$ units, and $R^3_2SiO_{2/2}$ units, or any combination thereof.

Each $R^3$ is a monovalent organic group exemplified by those described above for component (B). Alternatively, the monovalent organic groups represented by $R^3$ may have to 20 carbon atoms. Alternatively, examples of monovalent organic groups for $R^3$ include, but are not limited to, monovalent hydrocarbon groups and monovalent halogenated hydrocarbon groups.

The resin may contain an average of 3 to 30 mole percent of aliphatically unsaturated organic groups, alternatively 0.1 to 30 mole percent, alternatively 0.1 to 5 mole percent, alternatively 3 to 100 mole percent. The aliphatically unsaturated organic groups may be alkenyl groups, alkynyl groups, or a combination thereof. The mole percent of aliphatically unsaturated organic groups in the resin is the ratio of the number of moles of unsaturated group-containing siloxane units in the resin to the total number of moles of siloxane units in the resin, multiplied by 100.

Methods of preparing resins are well known in the art. For example, resin may be prepared by treating a resin copolymer produced by the silica hydrosol capping process of Daudt, et al. with at least an alkenyl-containing endblocking reagent. The method of Daudt et al., is disclosed in U.S. Pat. No. 2,676,182.

The method of Daudt, et al. involves reacting a silica hydrosol under acidic conditions with a hydrolyzable triorganosilane such as trimethylchlorosilane, a siloxane such as hexamethyldisiloxane, or mixtures thereof, and recovering a copolymer having M-units and Q-units. The resulting copolymers generally contain from 2 to 5 percent by weight of hydroxyl groups.

The resin, which typically contains less than 2% of silicon-bonded hydroxyl groups, may be prepared by treating the product of Daudt, et al. with an unsaturated organic group-containing endblocking agent and an endblocking agent free of aliphatic unsaturation, in an amount sufficient to provide from 3 to 30 mole percent of unsaturated organic groups in the final product. Examples of endblocking agents include, but are not limited to, silazanes, siloxanes, and silanes. Suitable endblocking agents are known in the art and exemplified in U.S. Pat. Nos. 4,584,355; 4,591,622; and 4,585,836. A single endblocking agent or a mixture of such agents may be used to prepare the resin.

Alternatively, component (B) may comprise a silicon containing base polymer other than the polyorganosiloxanes described above. For example, other compounds suitable for component (B) include silazanes and/or polymeric materials containing silicon atoms joined together by hydrocarbyl groups such as alkylene or polyalkylene groups or arylene groups. The silicon-modified organic compounds useful as component (B) include organic polymers having at least one silicon atom attached as a silane or a siloxane segment. The silicon-containing units can contain aliphatic unsaturation and can be attached at the terminal and/or pendant positions on the organic polymer chain or as a copolymer. Other representative silicon-modified organic polymers for component (B) are exemplified by, but not limited to alkenylsiloxy-functional polymers such as vinylsiloxy-, allylsiloxy-, and hexenylsiloxy-organic polymers and siloxane-organic block copolymers. Examples of silane-modified organic polymers are silylated polymers derived from olefins, isomonoolefin, dienes, ethylene or propylene oxides, and vinyl aromatic monomers having 2 to 20 carbon atoms such as the silane-grafted copolymers of isomonoolefin and vinyl aromatic monomers.

Examples of silicon-modified organic polymers described by above include vinylsiloxy-terminated or hexenylsiloxy-terminated poly(dimethylsiloxane/hydrocarbyl) copolymers, vinylsiloxy-terminated or hexenylsiloxy-terminated poly(dimethylsiloxane/polyoxyalkylene) block copolymers, alkenyloxydimethylsiloxy-terminated polyisobutylene and alkenyloxydimethylsiloxy-terminated polydimethylsiloxane/polyisobutylene block copolymers. Examples of suitable compounds for component (B) may be found, for example, in WO 2003/093369.

The amount of component (B) in the composition depends on various factors including the desired form of the reaction product of the composition, the quantity and hydrosilylation reactivity of the aliphatically unsaturated groups of component (B), the type and amount of component (A), and the content of silicon bonded hydrogen atoms of, component (B) and/or component (C). However, the amount of component (B) may range from 0.1% to 99.9% based on the weight of all components in the composition.

Component (C) in the composition is a Si—H functional compound, i.e., a compound having an average, per molecule, of one or more silicon bonded hydrogen atoms. Component (C) may comprise a silane and/or an organohydrogensilicon compound. Alternatively, component (C) may have an average, per molecule, of at least two silicon-bonded hydrogen atoms. The amount of component (C) in the composition depends on various factors including the SiH content of component (C), the unsaturated group content of component (B), and the properties of the reaction product of the composition desired, however, the amount of component (C) may be sufficient to provide a molar ratio of SiH groups in component (C) to aliphatically unsaturated organic groups in component (B) (commonly referred to as the SiH:Vi ratio) ranging from 0.3:1 to 5:1, alternatively 0.1:10 to 10:1. Component (C) can have a monomeric or polymeric structure. When component (C) has a polymeric structure, the polymeric structure may be linear, branched, cyclic, or resinous structure. When component (C) is polymeric, then component (C) can be a homopolymer or a copolymer. The silicon-bonded hydrogen atoms in component (C) can be located at terminal, pendant, or at both terminal and pendant positions. Component (C) may be one SiH functional compound. Alternatively, component (C) may comprise a combination of two or more SiH functional compounds. Component (C) may be two or more organohydrogenpolysiloxanes that differ in at least one of the following properties: structure, average molecular weight, viscosity, siloxane units, and sequence.

In certain embodiments, component (C) may comprise a silane of formula (5): $R^4_e SiH_f$, where subscript e is 0, 1, 2, or 3; subscript f is 1, 2, 3, or 4, with the proviso that a sum of (e+f) is 4. Each $R^4$ is independently a halogen atom or a monovalent organic group. Suitable halogen atoms for $R^4$ are exemplified by chlorine, fluorine, bromine, and iodine; alternatively chlorine. Suitable monovalent organic groups for $R^4$ include, but are not limited to, monovalent hydrocarbon and monovalent halogenated hydrocarbon groups. Monovalent hydrocarbon groups include, but are not limited to, alkyl such Me, Et, Pr, Bu, pentyl, hexyl, heptyl, octyl, decyl, dodecyl, undecyl, and octadecyl; cycloalkyl such as cyclopentyl and cyclohexyl; aryl such as Ph, tolyl, xylyl, and naphthyl; and aralkyl such as benzyl, 1-phenylethyl and 2-phenylethyl. Examples of monovalent halogenated hydrocarbon groups include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups include, but are not limited to, hydrocarbon groups substituted with oxygen atoms such as glycidoxyalkyl, and alkoxy groups such as methoxy, ethoxy, propoxy, and butoxy; and hydrocarbon groups substituted with nitrogen atoms such as aminoalkyl and cyano-functional groups such as cyanoethyl and cyanopropyl. Examples of suitable silanes for component (C) are exemplified by trichlorosilane ($HSiCl_3$), $Me_2HSiCl$, or $MeHSi(OMe)_2$.

Alternatively, the organohydrogensilicon compound of component (C) may comprise a polyorganohydrogensiloxane comprising siloxane units including, but not limited to, $HR^5_2SiO_{1/2}$, $R^5_3SiO_{1/2}$, $HR^5SiO_{2/2}$, $R^5_2SiO_{2/2}$, $R^5SiO_{3/2}$, $HSiO_{3/2}$ and $SiO_{4/2}$ units. In the preceding formulae, each $R^5$ is independently selected from the monovalent organic groups free of aliphatic unsaturation described above.

In certain embodiments, component (C) may comprise a polyorganohydrogensiloxane of Formula (III): $R^5_3SiO(R^5_2SiO)_g(R^5HSiO)_hSiR^5_3$; Formula (IV): $R^5_2HSiO(R^5_2SiO)_i(R^5HSiO)_jSiR^5_2H$; or a combination thereof. In formulae (III) and (IV) above, subscript g has an average value ranging from 0 to 2000, subscript h has an average value ranging from 2 to 2000, subscript i has an average value ranging from 0 to 2000, and subscript j has an average value ranging from 0 to 2000. Each $R^5$ is independently a monovalent organic group, as described above.

Polyorganohydrogensiloxanes for component (C) are exemplified by:
a) dimethylhydrogensiloxy-terminated polydimethylsiloxane,
b) dimethylhydrogensiloxy-terminated poly(dimethylsiloxane/methylhydrogensiloxane),
c) dimethylhydrogensiloxy-terminated polymethylhydrogensiloxane,
d) trimethylsiloxy-terminated poly(dimethylsiloxane/methylhydrogensiloxane),
e) trimethylsiloxy-terminated polymethylhydrogensiloxane,
f) a resin consisting essentially of $H(CH_3)_2SiO_{1/2}$ units and $SiO_{4/2}$ units, and
g) any combination thereof.

Methods of preparing linear, branched, and cyclic organohydrogenpolysiloxanes suitable for use as component (C), such as hydrolysis and condensation of organohalosilanes, are well known in the art. Methods of preparing organohydrogenpolysiloxane resins suitable for use as component (C) are also well known as exemplified in U.S. Pat. Nos. 5,310,843; 4,370,358; and 4,707,531.

Alternatively, the organohydrogensilicon compound of component (C) may comprise a compound of formula (V):

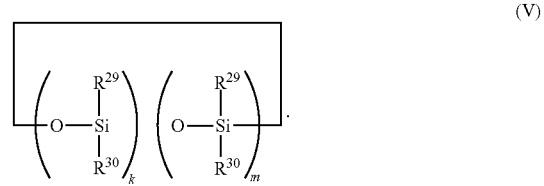

where each $R^{29}$ is independently selected from a hydrogen atom and a monovalent organic group comprising 1 to 20 member atoms, subscript k is an integer with a value ranging from 4-0 to 18, subscript m is an integer with a value ranging from 0 to 19, k+m is an integer with a value ranging from 3 to 20, alternatively 3 to 40. Each $R^{30}$ is independently selected from a monovalent organic group a halogen atom or a siloxane unit as described in the sections above. Alternatively each $R^{30}$ is a functional group independently selected from a halogen atom, an ether group, an alkoxy group, an alkoxyether group, an acyl group, an epoxy group, an amino group, a silyl group, or a —Z—$R^{31}$ group, where each Z is independently selected from an oxygen atom and a divalent hydrocarbon group comprising 2 to 20 carbon atoms, each $R^{31}$ group is independently selected from —$BR^{29}_u R^{32}_{2-u}$, —Si $R^{29}_v R^{32}_{3-v}$, or a group described by formula (VI): $(R^{32}_{3-n}R^{29}_n SiO_{1/2})_w(R^{32}_{2-o}R^{29}_o SiO_{2/2})_x(R^{32}_{1-p}R^{29}_p SiO_{3/2})_y (SiO_{4/2})_z(CR^{29}_q R^{32}_{1-q})_{aa}(CR^{29}_r R^{32}_{2-r})_{bb}(O(CR^{29}_s R^{32}_{2-s})_{cc} (CR^{29}_t R^{32}_{3-t})_{dd}$, where B refers to boron, each $R^{29}$ is as described above, the sum of w+x+y+z+aa+bb+cc+dd is at least 2, subscript n is an integer with a value ranging from 0 to 3, subscript o is an integer with a value ranging from 0 to 2, subscript p is an integer with a value ranging from 0 to 1, subscript q is an integer with a value ranging from 0 to 1, subscript r is an integer with a value ranging from 0 to 2, subscript s is an integer with a value ranging from 0 to 2, subscript t is an integer with a value ranging from 0 to 3, subscript u is an integer with a value ranging from 0 to 2, subscript v is an integer with a value ranging from 0 to 3, each $R^{32}$ is a functional group independently selected from a halogen atom, an ether group, an alkoxy group, an alkoxyether group, an acyl group, an epoxy group, an amino group, a silyl group, or a Z-Ggroup, where Z is as described above, each G is a cyclosiloxane described by formula (VII):

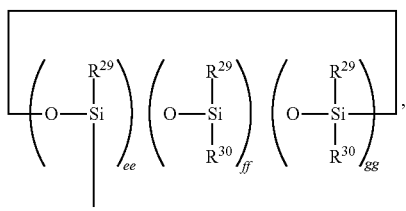

(VII)

where $R^{29}$ and $R^{30}$ are as described above, subscript ee is 1, subscript ff is an integer with a value ranging from 0 to 18, subscript gg is an integer with a value ranging from 0 to 18, ff+gg is an integer with a value ranging from 2 to 20, provided in formula (VII) that one of the $R^{32}$ groups is replaced by the Z group bonding the $R^{31}$ group to the cyclosiloxane of formula (VII), and provided further if aa+bb+cc+dd>0 then w+x+y+z>0.

Such organohydrogensilicon compounds are commercially available and methods for their preparation are exemplified in WO2003/093349 and WO2003/093369. An exemplary organohydrogensilicon compound may have the general formula:

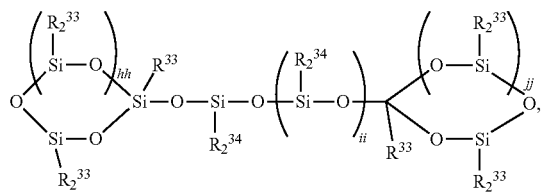

where each $R^{33}$ is independently selected from a hydrogen atom and a monovalent organic group; each $R^{34}$ is independently selected from a hydrogen atom, a monovalent organic group, and
a group of formula:

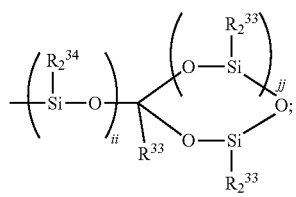

subscript hh is an integer with a value of at least 1; subscript jj is an integer with a value of at least 1; and subscript ii is an integer with a minimum value of 0. In the general formula, at least one instance of $R^{33}$ is a hydrogen atom. Suitable monovalent organic groups for $R^{33}$ and/or $R^{34}$ are exemplified by those groups described above for $R^{29}$.

The exact amount of component (C) in the composition depends on various factors including reactivity of component (A), the type and amount of component (B), whether component (B) contains a silicon bonded hydrogen atom, and the type and amount of any additional component (other than component (C)), if present. However, the amount of component (C) in the composition may range from 0% to 25%, alternatively 0.1% to 15%, and alternatively 1% to 5%, based on total weight of all components in the composition.

Component (D) is a spacer. Spacers can comprise organic particles, inorganic particles, or a combination thereof. Spacers can be thermally conductive, electrically conductive, or both. Spacers can have a desired particle size, for example, particle size may range from 25 micrometers (μm) to 125 μm. Spacers can comprise monodisperse beads, such as glass or polymer (e.g., polystyrene) beads. Spacers can comprise thermally conductive fillers such as alumina, aluminum nitride, atomized metal powders, boron nitride, copper, and silver. The amount of component (D) depends on various factors including the particle size distribution, pressure to be applied during use of the composition or the cured product prepared therefrom, temperature during use, and desired thickness of the composition or the cured product prepared therefrom. However, the composition may contain an amount of component (D) ranging from 0.05% to 2%, alternatively 0.1% to 1%.

Component (E) is an extender and/or a plasticizer. An extender comprising a non-functional polyorganosiloxane may be used in the composition. For example, the non-functional polyorganosiloxane may comprise difunctional units of the formula: $R^6_2SiO_{2/2}$ and terminal units of the formula: $R^7_3SiR^{28}$—, where each $R^6$ and each $R^7$ are independently a monovalent organic group such as a monovalent hydrocarbon group exemplified by alkyl such as methyl, ethyl, propyl, and butyl; alkenyl such as vinyl, allyl, and hexenyl; aryl such as Ph, tolyl, xylyl, and naphthyl; and aralkyl groups such as phenylethyl; and $R^{28}$ is an oxygen atom or a divalent group linking the silicon atom of the terminal unit with another silicon atom. The divalent linking group for $R^{28}$ may be a divalent organic group, a silicone organic group, or a combination of a divalent hydrocarbon group and a divalent siloxane group. Alternatively, each $R^{28}$ may be independently selected from an oxygen atom and a divalent hydrocarbon group. Alternatively, each $R^{28}$ may be an oxygen atom. Alternatively, each $R^{28}$ may be a divalent hydrocarbon group exemplified by an alkylene group such as ethylene, propylene, butylene, or hexylene; an arylene group such as phenylene, or an alkylarylene group such as:

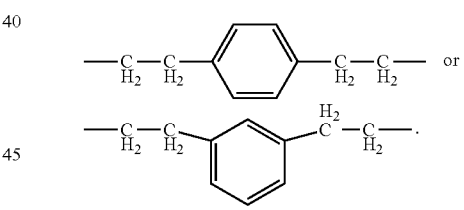

Alternatively, an instance of $R^{28}$ may be an oxygen atom while a different instance of $R^{28}$ is a divalent hydrocarbon group. Non-functional polyorganosiloxanes are known in the art and are commercially available. Suitable non-functional polyorganosiloxanes are exemplified by, but not limited to, polydimethylsiloxanes. Such polydimethylsiloxanes include DOW CORNING® 200 Fluids, which are commercially available from Dow Corning Corporation of Midland, Mich., U.S.A. and may have viscosity ranging from 50 cSt to 100,000 cSt, alternatively 50 cSt to 50,000 cSt, and alternatively 12,500 cSt to 60,000 cSt.

An organic plasticizer may be used in addition to, or instead of, the non-functional polyorganosiloxane extender described above. Organic plasticizers are known in the art and are commercially available. The organic plasticizer may comprise a phthalate, a carboxylate, a carboxylic acid ester, an adipate or a combination thereof. The organic plasticizer may be selected from the group consisting of: bis(2-ethylhexyl) terephthalate; bis(2-ethylhexyl)-1,4-benzenedicarboxylate; 2-ethylhexyl methyl-1,4-benzenedicarboxylate; 1,2 cyclohexanedicarboxylic acid, dinonyl ester, branched and linear; bis(2-propylheptyl) phthalate; diisononyl adipate; and a combination thereof.

The organic plasticizer may have an average, per molecule, of at least one group of formula:

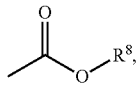

where $R^8$ represents a hydrogen atom or a monovalent organic group. Alternatively, $R^8$ may represent a branched or linear monovalent hydrocarbon group. The monovalent organic group may be a branched or linear monovalent hydrocarbon group such as an alkyl group of 4 to 15 carbon atoms, alternatively 9 to 12 carbon atoms. Suitable plasticizers may be selected from the group consisting of adipates, carboxylates, phthalates, and a combination thereof.

Alternatively, the organic plasticizer may have an average, per molecule, of at least two groups of the formula above bonded to carbon atoms in a cyclic hydrocarbon. The organic plasticizer may have general formula:

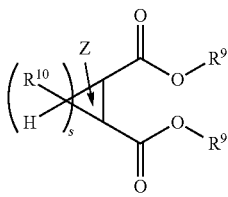

In this formula, group Z represents a cyclic hydrocarbon group having 3 or more carbon atoms, alternatively 3 to 15 carbon atoms. Subscript k may have a value ranging from 1 to 12. Group Z may be saturated or aromatic. Each $R^{10}$ is independently a hydrogen atom or a branched or linear monovalent organic group. The monovalent organic group for $R^9$ may be an alkyl group such as Me, Et, or Bu. Alternatively, the monovalent organic group for $R^{10}$ may be an ester functional group. Each $R^9$ is independently a branched or linear monovalent hydrocarbon group, such as an alkyl group of 4 to 15 carbon atoms.

Suitable organic plasticizers are known in the art and are commercially available. The plasticizer may comprise a phthalate, such as: a dialkyl phthalate such as dibutyl phthalate (Eastman™ DBP Plasticizer), diheptyl phthalate, di(2-ethylhexyl) phthalate, or diisodecyl phthalate (DIDP), bis(2-propylheptyl) phthalate (BASF Palatinol® DPHP), di(2-ethylhexyl) phthalate (Eastman™ DOP Plasticizer), dimethyl phthalate (Eastman™ DMP Plasticizer); diethyl phthalate (Eastman™ DMP Plasticizer); butyl benzyl phthalate, and bis(2-ethylhexyl) terephthalate (Eastman™ 425 Plasticizer); a dicarboxylate such as Benzyl, C7-C9 linear and branched alkyl esters, 1, 2, benzene dicarboxylic acid (Ferro SANTICIZER® 261A), 1,2,4-benzenetricarboxylic acid (BASF Palatinol® TOTM-I), bis(2-ethylhexyl)-1,4-benzenedicarboxylate (Eastman™ 168 Plasticizer); 2-ethylhexyl methyl-1,4-benzenedicarboxylate; 1,2 cyclohexanedicarboxylic acid, dinonyl ester, branched and linear (BASF Hexamoll *DINCH); diisononyl adipate; trimellitates such as trioctyl trimellitate (Eastman™ TOTM Plasticizer); triethylene glycol bis(2-ethylhexanoate) (Eastman™ TEG-EH Plasticizer); triacetin (Eastman™ Triacetin); nonaromatic dibasic acid esters such as dioctyl adipate, bis(2-ethylhexyl) adipate (Eastman™ DOA Plasticizer and Eastman™ DOA Plasticizer, Kosher), di-2-ethylhexyladipate (BASF Plastomoll® DOA), dioctyl sebacate, dibutyl sebacate and diisodecyl succinate; aliphatic esters such as butyl oleate and methyl acetyl recinolate; phosphates such as tricresyl phosphate and tributyl phosphate; chlorinated paraffins; hydrocarbon oils such as alkyldiphenyls and partially hydrogenated terphenyls; process oils; epoxy plasticizers such as epoxidized soybean oil and benzyl epoxystearate; tris(2-ethylhexyl) ester; a fatty acid ester; and a combination thereof. Examples of other suitable plasticizers and their commercial sources include BASF Palamoll® 652 and Eastman 168 Xtreme™ Plasticizer.

Alternatively, a polymer plasticizer can be used. Examples of the polymer plasticizer include alkenyl polymers obtained by polymerizing vinyl or allyl monomers by means of various methods; polyalkylene glycol esters such as diethylene glycol dibenzoate, triethylene glycol dibenzoate and pentaerythritol ester; polyester plasticizers obtained from dibasic acids such as sebacic acid, adipic acid, azelaic acid and phthalic acid and dihydric alcohols such as ethylene glycol, diethylene glycol, triethylene glycol, propylene glycol and dipropylene glycol; polyethers including polyether polyols each having a molecular weight of not less than 500 such as polyethylene glycol, polypropylene glycol and polytetramethylene glycol, polystyrenes such as polystyrene and poly-alpha-methylstyrene; and polybutadiene, polybutene, polyisobutylene, butadiene acrylonitrile, and polychloroprene.

The polyorganosiloxane extenders and organic plasticizers described above for component (E) may be used either each alone or in combinations of two or more thereof. A low molecular weight organic plasticizer and a higher molecular weight polymer plasticizer may be used in combination. The exact amount of component (E) used in the composition will depend on various factors including the desired end use of the composition and the cured product thereof. However, the amount of component (E) may range from 0.1% to 10% based on the combined weights of all components in the composition.

Component (F) is a filler. The filler may comprise a reinforcing filler, an extending filler, a conductive filler, or a combination thereof. For example, the composition may optionally further comprise component (f1), a reinforcing filler, which when present may be added in an amount ranging from 0.1% to 95%, alternatively 1% to 60%, based on the weight of the composition. The exact amount of component (f1) depends on various factors including the form of the reaction product of the composition (e.g., gel or rubber) and whether any other fillers are added. Examples of suitable reinforcing fillers include chopped fiber such as chopped KEVLAR®, and/or reinforcing silica fillers such as fume silica, silica aerogel, silica xerogel, and precipitated silica. Fumed silicas are known in the art and commercially available; e.g., fumed silica sold under the name CAB-O-SIL by Cabot Corporation of Massachusetts, U.S.A.

The composition may optionally further comprise component (f2) an extending filler in an amount ranging from 0.1% to 95%, alternatively 1% to 60%, and alternatively 1% to 20%, based on the weight of the composition. Examples of extending fillers include crushed quartz, aluminum oxide, magnesium oxide, calcium carbonate such as precipitated calcium carbonate, zinc oxide, talc, diatomaceous earth, iron oxide, clays, mica, titanium dioxide, zirconia, sand, carbon black, graphite, or a combination thereof. Extending fillers are known in the art and commercially available; such as a ground silica sold under the name MIN-U-SIL by U.S. Silica of Berkeley Springs, W. Va. Suitable precipitated calcium carbonates included Winnofil® SPM from Solvay and Ultrapflex® and Ultrapflex® 100 from SMI.

The composition may optionally further comprise component (f3) a conductive filler. Component (F) may be both thermally conductive and electrically conductive. Alternatively, component (F) may be thermally conductive and electrically insulating. Component (F) may be selected from the group consisting of aluminum nitride, aluminum oxide, aluminum trihydrate, barium titanate, beryllium oxide, boron nitride, carbon fibers, diamond, graphite, magnesium hydroxide, magnesium oxide, metal particulate, onyx, silicon carbide, tungsten carbide, zinc oxide, and a combination thereof. Component (F) may comprise a metallic filler, an inorganic filler, a meltable filler, or a combination thereof. Metallic fillers include particles of metals and particles of metals having layers on the surfaces of the particles. These layers may be, for example, metal nitride layers or metal oxide layers on the surfaces of the particles. Suitable metallic fillers are exemplified by particles of metals selected from the group consisting of aluminum, copper, gold, nickel, silver, and combinations thereof, and alternatively aluminum. Suitable metallic fillers are further exemplified by particles of the metals listed above having layers on their surfaces selected from the group consisting of aluminum nitride, aluminum oxide, copper oxide, nickel oxide, silver oxide, and combinations thereof. For example, the metallic filler may comprise aluminum particles having aluminum oxide layers on their surfaces.

Inorganic conductive fillers are exemplified by onyx; aluminum trihydrate, metal oxides such as aluminum oxide, beryllium oxide, magnesium oxide, and zinc oxide; nitrides such as aluminum nitride and boron nitride; carbides such as silicon carbide and tungsten carbide; and combinations thereof. Alternatively, inorganic conductive fillers are exemplified by aluminum oxide, zinc oxide, and combinations thereof. Meltable fillers may comprise Bi, Ga, In, Sn, or an alloy thereof. The meltable filler may optionally further comprise Ag, Au, Cd, Cu, Pb, Sb, Zn, or a combination thereof. Examples of suitable meltable fillers include Ga, In—Bi—Sn alloys, Sn—In—Zn alloys, Sn—In—Ag alloys, Sn—Ag—Bi alloys, Sn—Bi—Cu—Ag alloys, Sn—Ag—Cu—Sb alloys, Sn—Ag—Cu alloys, Sn—Ag alloys, Sn—Ag—Cu—Zn alloys, and combinations thereof. The meltable filler may have a melting point ranging from 50° C. to 250° C., alternatively 150° C. to 225° C. The meltable filler may be a eutectic alloy, a non-eutectic alloy, or a pure metal. Meltable fillers are commercially available.

For example, meltable fillers may be obtained from Indium Corporation of America. Utica, N.Y., U.S.A.; Arconium, Providence, R.I., U.S.A.; and AIM Solder, Cranston, R.I., U.S.A. Aluminum fillers are commercially available, for example, from Toyal America, Inc. of Naperville, Ill., U.S.A. and Valimet Inc., of Stockton, Calif., U.S.A. Silver filler is commercially available from Metalor Technologies U.S.A. Corp. of Attleboro, Mass., U.S.A.

Thermally conductive fillers are known in the art and commercially available. For example, CB-A20S and AI-43-Me are aluminum oxide fillers of differing particle sizes commercially available from Showa-Denko, and AA-04, AA-2, and AA18 are aluminum oxide fillers commercially available from Sumitomo Chemical Company. Zinc oxides, such as zinc oxides having trademarks KADOX® and XX®, are commercially available from Zinc Corporation of America of Monaca, Pa., U.S.A.

The shape of the filler particles is not specifically restricted, however, rounded or spherical particles may prevent viscosity increase to an undesirable level upon high loading of the filler in the composition.

Component (F) may be a single filler or a combination of two or more fillers that differ in at least one property such as particle shape, average particle size, particle size distribution, and type of filler. For example, it may be desirable to use a combination of fillers, such as a first filler having a larger average particle size and a second filler having a smaller average particle size. Use of a first filler having a larger average particle size and a second filler having a smaller average particle size than the first filler may improve packing efficiency and/or may reduce viscosity of the composition as compared to a composition without such a combination of fillers.

The average particle size of the filler will depend on various factors including the type of the filler selected for component (F) and the exact amount added to the composition, as well as the end use for the reaction product of the composition. However, the filler may have an average particle size ranging from 0.1 to 80 µm, alternatively 0.1 to 50 µm, and alternatively 0.1 to 10 µm.

The amount of component (F) in the composition depends on various factors including the end use selected for the composition and the reaction product of the composition, the type and amount of component (B), and the type and amount of the filler selected for component (F). However, the amount of component (F) may range from 0 vol % to 80 vol %, alternatively 50 vol % to 75 vol %, and alternatively 30% to 80%, by volume of the composition. Without wishing to be bound by theory, it is thought that when the amount of filler is greater than 80 vol %, the composition may react to form a reaction product with insufficient dimensional integrity for some applications.

The composition may optionally further comprise component (G) a treating agent. The amount of component (G) will vary depending on factors such as the type of treating agent selected and the type and amount of particulates (such as components (F) and/or (D)) to be treated, and whether the particulates are treated before being added to the composition, or whether the particulates are treated in situ. However, component (G) may be used in an amount ranging from 0.01% to 20%, alternatively 0.1% to 15%, and alternatively 0.5% to 5%, based on the weight of all components in the composition. Particulates, such as the filler, the physical drying agent, certain flame retardants, and/or certain pigments, when present, may optionally be surface treated with component (G). Particulates may be treated with component (G) before being added to the composition, or in situ. Component (G) may comprise an alkoxysilane, an alkoxyfunctional oligosiloxane, a cyclic polyorganosiloxane, a hydroxyl-functional oligosiloxane such as a dimethyl siloxane or methyl phenyl siloxane, or a fatty acid. Examples of fatty acids include stearates such as calcium stearate.

Some representative organosilicon filler treating agents that can be used as component (G) include compositions normally used to treat silica fillers such as organochlorosilanes, organosiloxanes, organodisilazanes such as hexaalkyl disilazane, and organoalkoxysilanes such as $C_6H_{13}Si(OCH_3)_3$, $C_8H_{17}Si(OC_2H_5)_3$, $C_{10}H_{21}Si(OCH_3)_3$, $C_{12}H_{25}Si(OCH_3)_3$, $C_{14}H_{29}Si(OC_2H_5)_3$, and $C_6H_5CH_2CH_2Si(OCH_3)_3$. Other treating agents that can be used include alkylthiols, fatty acids, titanates, titanate coupling agents, zirconate coupling agents, and combinations thereof.

Alternatively, component (G) may comprise an alkoxysilane having the formula: $R^{11}{}_mSi(OR^{12})_{(4-m)}$, where subscript m may have a value ranging from 1 to 3, alternatively subscript m is 3. Each $R^{11}$ is independently a monovalent organic group, such as a monovalent hydrocarbon group of 1 to 50 carbon atoms, alternatively 8 to 30 carbon atoms, alternatively 8 to 18 carbon atoms. $R^{11}$ is exemplified by alkyl groups such as hexyl, octyl, dodecyl, tetradecyl, hexadecyl, and octadecyl; and aromatic groups such as benzyl and phenylethyl. $R^{11}$ may be saturated or unsaturated, and branched or unbranched. Alternatively, $R^{11}$ may be saturated and unbranched.

Each $R^{12}$ is independently a saturated hydrocarbon group of 1 to 4 carbon atoms, alternatively 1 to 2 carbon atoms. Alkoxysilanes suitable for use as component (G) are exemplified by hexyltrimethoxysilane, octyltriethoxysilane, decyltrimethoxysilane, dodecyltrimethoxysilane, tetradecyltrimethoxysilane, phenylethyltrimethoxysilane, octadecyltrimethoxysilane, octadecyltriethoxysilane, and combinations thereof.

Alkoxy-functional oligosiloxanes may also be used as treating agents. For example, suitable alkoxy-functional oligosiloxanes include those of the formula (V): $(R^{13}O)_n Si(OSiR^{14}_2 R^{15})_{(4-n)}$. In this formula, subscript n is 1, 2 or 3, alternatively subscript n is 3. Each $R^{13}$ may be an alkyl group. Each $R^{14}$ may be an unsaturated monovalent hydrocarbon group of 1 to 10 carbon atoms. Each $R^{15}$ may be an unsaturated monovalent hydrocarbon group having at least 10 carbon atoms.

Certain particulates, such as metal fillers may be treated with alkylthiols such as octadecyl mercaptan; fatty acids such as oleic acid and stearic acid; and a combination thereof.

Treatment agents for alumina or passivated aluminum nitride may include alkoxysilyl functional alkylmethyl polysiloxanes (e.g., partial hydrolysis condensate of $R^{16}_o R^{17}_p Si(OR^{18})_{(4-o-p)}$ or cohydrolysis condensates or mixtures), or similar materials where the hydrolyzable group may comprise silazane, acyloxy or oximo. In all of these, a group tethered to Si, such as $R^{16}$ in the formula above, is a long chain unsaturated monovalent hydrocarbon or monovalent aromatic-functional hydrocarbon. Each $R^{17}$ is independently a monovalent hydrocarbon group, and each $R^{18}$ is independently a monovalent hydrocarbon group of 1 to 4 carbon atoms. In the formula above, subscript o is 1, 2, or 3 and subscript p is 0, 1, or 2, with the proviso that a sum (o+p) is 1, 2, or 3.

Other treating agents include alkenyl functional polyorganosiloxanes. Suitable alkenyl functional polyorganosiloxanes include, but are not limited to:

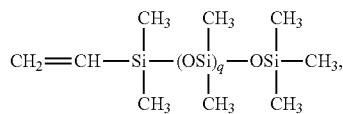

where subscript q has a value up to 1,500. Other treating agents include mono-endcapped alkoxy functional polydiorganosiloxanes. i.e., polydiorganosiloxanes having an alkoxy group at one end. Such treating agents are exemplified by the formula: $R^{25}R^{26}_2 SiO(R^{26}_2 SiO)_u Si(OR^{27})_3$, where subscript u has a value of 0 to 100, alternatively to 50, alternatively 1 to 10, and alternatively 3 to 6. Each $R^{25}$ is independently selected from an alkyl group, such as Me, Et, Pr, Bu, hexyl, and octyl; and an alkenyl group, such as Vi, allyl, butenyl, and Hex. Each $R^{26}$ is independently an alkyl group such as Me, Et, Pr, Bu, hexyl, and octyl. Each $R^{27}$ is independently an alkyl group such as Me, Et, Pr, and Bu. Alternatively, each $R^{25}$, each $R^{26}$, and each $R^{27}$ is Me. Alternatively, each $R^{25}$ is Vi. Alternatively, each $R^{26}$ and each $R^{27}$ is Me.

Alternative, a polyorganosiloxane capable of hydrogen bonding is useful as a treating agent. This strategy to treating surface of a filler takes advantage of multiple hydrogen bonds, either clustered or dispersed or both, as the means to tether the compatibilization moiety to the filler surface. The polyorganosiloxane capable of hydrogen bonding has an average, per molecule, of at least one silicon-bonded group capable of hydrogen bonding. The group may be selected from: an organic group having multiple hydroxyl functionalities or an organic group having at least one amino functional group. The polyorganosiloxane capable of hydrogen bonding means that hydrogen bonding is the primary mode of attachment for the polyorganosiloxane to a filler. The polyorganosiloxane may be incapable of forming covalent bonds with the filler. The polyorganosiloxane capable of hydrogen bonding may be selected from the group consisting of a saccharide-siloxane polymer, an amino-functional polyorganosiloxane, and a combination thereof. Alternatively, the polyorganosiloxane capable of hydrogen bonding may be a saccharide-siloxane polymer.

Component (H) is a biocide. The amount of component (H) will vary depending on factors including the type of biocide selected and the benefit desired. However, the amount of component (H) may range from greater than 0% to 5% based on the weight of all components in the composition. Component (H) is exemplified by (h1) a fungicide, (h2) an herbicide, (h3) a pesticide, (h4) an antimicrobial agent, or a combination thereof.

Component (h1) is a fungicide, for example, these include N-substituted benzimidazole carbamate, benzimidazolyl carbamate such as methyl 2-benzimidazolylcarbamate, ethyl 2-benzimidazolylcarbamate, isopropyl 2-benzimidazolylcarbamate, methyl N-{2-[1-(N,N-dimethylcarbamoyl)benzimidazolyl]}carbamate, methyl N-{2-[1-(N,N-dimethylcarbamoyl)-6-methylbenzimidazolyl]}carbamate, methyl N-{2-[1-(N,N-dimethylcarbamoyl)-5-methylbenzimidazolyl]}carbamate, methyl N-{2-[1-(N-methylcarbamoyl)benzimidazolyl]}carbamate, methyl N-{2-[1-(N-methylcarbamoyl)-6-methylbenzimidazolyl]}carbamate, methyl N-{2-[1-(N-methylcarbamoyl-5-methylbenzimidazolyl]} carbamate, ethyl N-{2-[1-(N,N-dimethylcarbamoyl)benzimidazolyl]}carbamate, ethyl N-{2-[2-(N-methylcarbamoyl)benzimidazolyl]}carbamate, ethyl N-{2-[1-(N,N-dimethylcarbamoyl)-6-methylbenzimidazolyl]}carbamate, ethyl N-{2-[1-(N-methylcarbamoyl)-6-methylbenzimidazolyl]}carbamate, isopropyl N-{2-[1-(N,N-dimethylcarbamoyl)benzimidazolyl]}carbamate, isopropyl N-{2-[1-(N-methylcarbamoyl)benzimidazolyl])carbamate, methyl N-{2-[1-(N-propylcarbamoyl)benzimidazolyl]})carbamate, methyl N-{2-[1-(N-butylcarbamoyl)benzimidazolyl]}carbamate, methoxyethyl N-{2-[1-(N-propylcarbamoyl)benzimidazolyl]}carbamate, methoxyethyl N-{2-[1-(N-butylcarbamoyl)benzimidazolyl]}carbamate, ethoxyethyl N-{2-[1-(N-propylcarbamoyl)benzimidazolyl]}carbamate, ethoxyethyl N-{2-[1-(N-butylcarbamoyl)benzimidazolyl]} carbamate, methyl N-{1-(N,N-dimethylcarbamoyloxy)benzimidazolyl]}carbamate, methyl N-{2-[N-methylcarbamoyloxy)benzimidazolyl]}carbamate, methyl N-{2-[1-(N-butylcarbamoyloxy)benzoimidazolyl]}carbamate, ethoxyethyl N-{2-[1-(N-propylcarbamoyl)benzimidazolyl]} carbamate, ethoxyethyl N-{2-[1-(N-butylcarbamoyloxy)benzoimidazolyl]}carbamate, methyl N-{2-[1-(N,N-dimethylcarbamoyl)-6-chlorobenzimidazolyl]}carbamate, and methyl N-{2-[1-(N,N-dimethylcarbamoyl)-6-nitrobenzimidazolyl]}carbamate; 10, 10'-oxybisphenoxarsine (which has trade name Vinyzene, OBPA), di-iodomethyl-para-tolylsulfone, benzothiophene-2-cyclohexylcarboxamide-S,S-dioxide, N-(fluordichloridemethylthio)phthalimide (which has trade names Fluor-Folper, and Preventol A3); methyl-benzimideazol-2-ylcarbamate (which has trade names Carbendazim, and Preventol BCM), zinc-bis(2-pyridylthio-1-oxide) (zinc pyrithion) 2-(4-thiazolyl)-benzimidazol, N-phenyl-iodpropargylcarbamate, N-octyl-4-isothiazolin-3-on, 4,5-dichloride-2-n-octyl-4-isothiazolin-3-on, N-butyl-1,2-benzisothiazolin-3-on and/or triazolyl-compounds, such as tebuconazol in combination with zeolites containing silver.

Component (h2) is an herbicide, for example, suitable herbicides include amide herbicides such as allidochlor N,N-diallyl-2-chloroacetamide; CDEA 2-chloro-N,N-diethylacetamide; etnipromid (RS)-2-[5-(2,4-dichlorophenoxy)-2-nitrophenoxy]-N-ethylpropionamide; anilide herbicides such ascisanilide cis-2,5-dimethylpyrrolidine-1-carboxanilide; flufenacet 4'-fluoro-N-isopropyl-2-[5-(trifluoromethyl)-1,3,4-thiadiazol-2-yloxy]acetanilide; naproanilide (RS)-α-2-naphthoxypropionanilide; arylalanine herbicides such asbenzoylprop N-benzoyl-N-(3,4-dichlorophenyl)-DL-alanine; flamprop-M N-benzoyl-N-(3-chloro-4-fluorophenyl)-D-alanine; chloroacetanilide herbicides such asbutachlor N-butoxymethyl-2-chloro-2',6'-diethylacetanilide; metazachlor 2-chloro-N-(pyrazol-1-ylmethyl)acet-2',6'-xylidide; prynachlor (RS)-2-chloro-N-(1-methylprop-2-ynyl)acetanilide; sulphonanilide herbicides such ascioransulam 3-chloro-2-(5-ethoxy-7-fluoro[1,2,4]triazolo[1,5-c]pyrimidin-2-ylsulphonamido)benzoic acid; metosulam 2',6'-dichloro-5,7-dimethoxy-3'-methyl[1,2,4]triazolo[1,5-a]pyrimidine-2-sulphonanilide; antibiotic herbicides such asbilanafos 4-[hydroxy(methyl)phosphinoyl]-L-homoalanyl-L-alanyl-L-alanine; benzoic acid herbicides such aschloramben 3-amino-2,5-dichlorobenzoic acid; 2,3,6-TBA 2,3,6-trichlorobenzoic acid; pyrimidinyloxybenzoic acid herbicides such asbispyribac 2,6-bis(4,6-dimethoxypyrimidin-2-yloxy)benzoic acid; pyrimidinylthiobenzoic acid herbicides such aspyrithiobac 2-chloro-6-(4,6-dimethoxypyrimidin-2-ylthio)benzoic acid; phthalic acid herbicides such aschlorthaltetrachloroterephthalic acid; picolinic acid herbicides such asaminopyralid 4-amino-3,6-dichloropyridine-2-carboxylic acid; quinolinecarboxylic acid herbicides such asquinclorac 3,7-dichloroquinoline-8-carboxylic acid; arsenical herbicides such asCMA calcium bis(hydrogen methylarsonate); MAMA ammonium hydrogen methylarsonate; sodium arsenite; benzoylcyclohexanedione herbicides such asmesotrione 2-(4-mesyl-2-nitrobenzoyl)cyclohexane-1,3-dione; benzofuranyl alkylsulphonate herbicides such asbenfuresate 2,3-dihydro-3,3-dimethylbenzofuran-5-yl ethanesulphonate; carbamate herbicides such ascarboxazole methyl 5-tert-butyl-1,2-oxazol-3-ylcarbamate; fenasulam methyl 4-[2-(4-chloro-o-tolyloxy)acetamido]phenylsulphonylcarbamate; carbanilate herbicides such asBCPC (RS)-seo-butyl 3-chlorocarbanilate; desmedipham ethyl 3-phenylcarbamoyloxyphenylcarbamate; swep methyl 3,4-dichlorocarbanilate; cyclohexene oxime herbicides such asbutroxydim (RS)-(EZ)-5-(3-butyryl-2,4,6-tnmethylphenyl)-2-(1-ethoxyiminopropyl)-3-hydroxycyclohex-2-en-1-one; tepraloxydim (RS)-(EZ)-2-{1-[(2E)-3-chloroallyloxyimino]propyl}-3-hydroxy-5-perhydropyran-4-ylcyclohex-2-en-1-one; cyclopropylisoxazole herbicides such asisoxachlortole 4-chloro-2-mesylphenyl 5-cyclopropyl-1,2-oxazol-4-yl ketone; dicarboximide herbicides such as flumezin 2-methyl-4-(α,α,α-trifluoro-m-tolyl)-1,2,4-oxadiazinane-3,5-dione; dinitroaniline herbicides such asethalfluralin N-ethyl-α,α,α-trifluoro-N-(2-methylallyl)-2,6-dinitro-p-toluidine; prodiamine 5-dipropylamino-α,α,α-trifluoro-4,6-dinitro-o-toluidine; dinitrophenol herbicides such as dinoprop 4,6-dinitro-o-cymen-3-ol; etinofen α-ethoxy-4,6-dinitro-o-cresol; diphenyl ether herbicides such asethoxyfen O-[2-chloro-5-(2-chloro-α,α,α-trifluoro-p-tolyloxy)benzoyl]-L-lactic acid; nitrophenyl ether herbicides such asaclonifen 2-chloro-6-nitro-3-phenoxyaniline; nitrofen 2,4-dichlorophenyl 4-nitrophenyl ether; dithiocarbamate herbicides such asdazomet 3,5-dimethyl-1,3,5-thiadiazinane-2-thione; halogenated aliphatic herbicides such as dalapon 2,2-dichloropropionic acid; chloroacetic acid; imidazolinone herbicides such as imazapyr (RS)-2-(4-isopropyl-4-methyl-5-oxo-2-imidazolin-2-yl)nicotinic acid; inorganic herbicides such as disodium tetraborate decahydrate; sodium azide; nitrile herbicides such as chloroxynil 3,5-dichloro-4-hydroxybenzonitrile; ioxynil 4-hydroxy-3,5-diiodobenzonitrile; organophosphorus herbicides such as anilofos S-4-chloro-N-isopropylcarbaniloylmethyl O,O-dimethyl phosphorodithioate; glufosinate 4-[hydroxy(methyl)phosphinoyl]-DL-homoalanine; phenoxy herbicides such as clomeprop (RS)-2-(2,4-dichloro-m-tolyloxy)propionanilide; fenteracol 2-(2,4,5-trichlorophenoxy)ethanol; phenoxyacetic herbicides such as MCPA (4-chloro-2-methylphenoxy)acetic acid; phenoxybutyric herbicides such as MCPB 4-(4-chloro-o-tolyloxy)butyric acid; phenoxypropionic herbicides such as fenoprop (RS)-2-(2,4,5-trichlorophenoxy)propionic acid; aryloxyphenoxypropionic herbicides such as isoxapyrifop (RS)-2-[2-[4-(3,5-dichloro-2-pyridyloxy)phenoxy]propionyl]isoxazolidine; phenylenediamine herbicides such as dinitramine $N^1,N^1$-diethyl-2,6-dinitro-4-trifluoromethyl-m-phenylenediamine, pyrazolyloxyacetophenone herbicides such as pyrazoxyfen 2-[4-(2,4-dichlorobenzoyl)-1,3-dimethylpyrazol-5-yloxy]acetophenone; pyrazolylphenyl herbicides such as pyraflufen 2-chloro-5-(4-chloro-5-difluoromethoxy-1-methylpyrazol-3-yl)-4-fluorophenoxyacetic acid: pyridazine herbicides such as pyridafol 6-chloro-3-phenylpyridazin-4-ol; pyridazinone herbicides such as chloridazon 5-amino-4-chloro-2-phenylpyridazin-3(2H)-one; oxapyrazon 5-bromo-1,6-dihydro-6-oxo-1-phenylpyridazin-4-yloxamic acid; pyridine herbicides such as fluroxypyr 4-amino-3,5-dichloro-6-fluoro-2-pyridyloxyacetic acid; thiazopyr methyl 2-difluoromethyl-5-(4,5-dihydro-1,3-thiazol-2-yl)-4-isobutyl-6-trifluoromethylnicotinate; pyrimidinediamine herbicides such as iprymidam 6-chloro-$N^4$-isopropylpyrimidine-2,4-diamine; quaternary ammonium herbicides such as diethamquat 1,1'-bis(diethylcarbamoylmethyl)-4,4'-bipyridinium; paraquat 1,1'-dimethyl-4,4'-bipyridinium; thiocarbamate herbicides such as cycloate S-ethyl cyclohexyl(ethyl)thiocarbamate; tiocarbazil S-benzyl di-sec-butylthiocarbamate; thiocarbonate herbicides such as EXD O,O-diethyl dithiobis(thioformate); thiourea herbicides such as methiuron 1,1-dimethyl-3-m-tolyl-2-thiourea; triazine herbicides such as triaziflam (RS)—N-[2-(3,5-dimethylphenoxy)-1-methylethyl-6-(1-fluoro-1-methylethyl)-1,3,5-triazine-2,4-diamine; chlorotriazine herbicides such as cyprazine 6-chloro-$N^2$-cyclopropyl-$N^4$-isopropyl-1,3,5-triazine-2,4-diamine; propazine 6-chloro-$N^2,N^4$-di-isopropyl-1,3,5-triazine-2,4-diamine; methoxytriazine herbicides such as prometon $N^2,N^4$-di-isopropyl-6-methoxy-1,3,5-triazine-2,4-diamine; methylthiotriazine herbicides such as cyanatryn 2-(4-ethylamino-6-methylthio-1,3,5-triazin-2-ylamino)-2-methylpropionitrile; triazinone herbicides such as hexazinone 3-cyclohexyl-6-dimethylamino-1-methyl-1,3,5-triazine-2,4(1H,3H)-dione; triazole herbicides such as epronaz N-ethyl-N-propyl-3-propylsulphonyl-1H-1,2,4-triazole-1-carboxamide; triazolone herbicides such as carfentrazone (RS)-2-chloro-3-{2-chloro-5-[4-(difluoromethyl)-4,5-dihydro-3-methyl-5-oxo-1H-1,2,4-triazol-1H-yl]-4-fluorophenyl}propionic acid; triazolopyrimidine herbicides such as florasulam 2',6',8-trifluoro-5-methoxy[1,2,4]triazolo[1,5-c]pyrimidine-2-sulphonanilide; uracil herbicides such as flupropacil isopropyl 2-chloro-5-(1,2,3,6-tetrahydro-3-methyl-2,6-dioxo-4-trifluoromethylpyrimidin-1-yl)benzoate; urea herbicides such as cycluron 3-cyclo-octyl-1,1-dimethylurea; monisouron 1-(5-tert-butyl-1,2-oxazol-3-yl)-3-methylurea; phenylurea herbicides such as chloroxuron 3-[4-(4-chlorophenoxy)phenyl]-1,1-dimethylurea; siduron 1-(2-methylcyclohexyl)-3-phenylurea; pyrimidinylsulphonylurea herbicides such as flazasulphuron 1-(4,6-dimethoxypyrimidin-2-yl)-3-(3-trifluoromethyl-2-pyridylsulphonyl)urea; pyrazosulphuron 5-[(4,6-dimethoxypyrimidin-2-ylcarbamoyl)sulphamoyl]-1-methylpyrazole-4-carboxylic acid; triazinylsulphonylurea herbicides such as thifensulphuron 3-(4-methoxy-6-methyl-1,3,5-triazin-2-ylcarbamoylsulphamoyl)thiophene-2-carboxylic acid; thiadiazolylurea herbicides such as tebuthiuron 1-(5-tert-butyl-1,3,4-thiadiazol-2-yl)-1,3-dimethylurea; and/or unclassified herbicides such as chlorfenac (2,3,6-trichlorophenyl)acetic acid; methazole 2-(3,4-dichlorophenyl)-4-methyl-1,2,4-oxadiazolidine-3,5-dione; tritac (RS)-1-(2,3,6-trichlorobenzyloxy)propan-2-ol; 2,4-D, chlorimuron, and fenoxaprop; and combinations thereof.

Component (h3) is a pesticide. Suitable pesticides are exemplified by atrazine, diazinon, and chlorpyrifos. For purposes of this application, pesticide includes insect repellents such as N,N-diethyl-meta-toluamide and pyrethroids such as pyrethrin.

Component (h4) is an antimicrobial agent. Suitable antimicrobials are commercially available, such as DOW CORNING® 5700 and DOW CORNING® 5772, which are from Dow Corning Corporation of Midland, Mich., U.S.A.

Alternatively, component (H) may comprise a boron containing material. e.g., boric anhydride, borax, or disodium octaborate tetrahydrate; which may function as a pesticide, fungicide, and/or flame retardant.

Component (I) is a stabilizer that may be used for altering the reaction rate of the composition, as compared to a composition containing the same components but with the stabilizer omitted. Stabilizers for hydrosilylation curable compositions are exemplified by acetylenic alcohols such as methyl butynol, ethynyl cyclohexanol, dimethyl hexynol, and 3,5-dimethyl-1-hexyn-3-ol, 1-butyn-3-ol, 1-propyn-3-ol, 2-methyl-3-butyn-2-ol, 3-methyl-1-butyn-3-ol, 3-methyl-1-pentyn-3-ol, 3-phenyl-1-butyn-3-ol, 4-ethyl-1-octyn-3-ol, 3,5-diemthyl-1-hexyn-3-ol, and 1-ethynyl-1-cyclohexanol, and a combination thereof; cycloalkenylsiloxanes such as methylvinylcyclosiloxanes exemplified by 1,3,5,7-tetramethyl-1,3,5,7-tetravinylcyclotetrasiloxane, 1,3,5,7-tetramethyl-1,3,5,7-tetrahexenylcyclotetrasiloxane, and a combination thereof; ene-yne compounds such as 3-methyl-3-penten-1-yne, 3,5-dimethyl-3-hexen-1-yne; triazoles such as benzotriazole; phosphines; mercaptans; hydrazines; amines, such as tetramethyl ethylenediamine, dialkyl fumarates, dialkenyl fumarates, dialkoxyalkyl fumarates, maleates such as diallyl maleate; nitriles; ethers; carbon monoxide; alkenes such as cyclo-octadiene, divinyltetramethyldisiloxane; alcohols such as benzyl alcohol; and a combination thereof.

Alternatively, component (I) in the composition may be a silylated acetylenic compound. Without wishing to be bound by theory, it is thought that adding a silylated acetylenic compound reduces yellowing of the reaction product prepared from hydrosilylation reaction of the composition as compared to a reaction product from hydrosilylation of a composition that does not contain a silylated acetylenic compound or that contains an organic acetylenic alcohol stabilizer, such as those described above.

The silylated acetylenic compound is exemplified by (3-methyl-1-butyn-3-oxy)trimethylsilane, ((1,1-dimethyl-2-propynyl)oxy)trimethylsilane, bis(3-methyl-1-butyn-3-oxy)dimethylsilane, bis(3-methyl-1-butyn-3-oxy)silanemethylvinylsilane, bis((1,1-dimethyl-2-propynyl)oxy)dimethylsilane, methyl(tris(1,1-dimethyl-2-propynyloxy))silane, methyl(tris(3-methyl-1-butyn-3-oxy))silane, (3-methyl-1-butyn-3-oxy)dimethylphenylsilane, (3-methyl-1-butyn-3-oxy)dimethylhexenylsilane, (3-methyl-1-butyn-3-oxy)triethylsilane, bis(3-methyl-1-butyn-3-oxy)methyltrifluoropropylsilane, (3,5-dimethyl-1-hexyn-3-oxy)trimethylsilane, (3-phenyl-1-butyn-3-oxy)diphenylmethylsilane, (3-phenyl-1-butyn-3-oxy)dimethylphenylsilane, (3-phenyl-1-butyn-3-oxy)dimethylvinylsilane, (3-phenyl-1-butyn-3-oxy)dimethylhexenylsilane, (cyclohexyl-1-ethyn-1-oxy)dimethylhexenylsilane, (cyclohexyl-1-ethyn-1-oxy)dimethylvinylsilane, (cyclohexyl-1-ethyn-1-oxy)diphenylmethylsilane, (cyclohexyl-1-ethyn-1-oxy)trimethylsilane, and combinations thereof. Alternatively, component (I) is exemplified by methyl(tris(1,1-dimethyl-2-propynyloxy))silane, ((1,1-dimethyl-2-propynyl)oxy)trimethylsilane, or a combination thereof. The silylated acetylenic compound useful as component (I) may be prepared by methods known in the art, such as silylating an acetylenic alcohol described above by reacting it with a chlorosilane in the presence of an acid receptor.

The amount of stabilizer added to the composition will depend on various factors including the desired pot life of the composition, whether the composition will be a one part composition or a multiple part composition, the particular stabilizer used, and the selection and amount of component (C), if present. However, when present, the amount of stabilizer may range from 0% to 1%, alternatively 0% to 5%, alternatively 0.001% to 1%, alternatively 0.01% to 0.5%, and alternatively 0.0025% to 0.025%, based on the weight of all components in the composition.

Component (J) is a flame retardant. Suitable flame retardants may include, for example, carbon black, hydrated aluminum hydroxide, and silicates such as wollastonite, platinum and platinum compounds. Alternatively, the flame retardant may be selected from halogen based flame-retardants such as decabromodiphenyloxide, octabromodiphenyl oxide, hexabromocyclododecane, decabromobiphenyl oxide, diphenyoxybenzene, ethylene bis-tetrabromophthalmide, pentabromoethyl benzene, pentabromobenzyl acrylate, tribromophenyl maleic imide, tetrabromobisphenyl A, bis-(tribromophenoxy) ethane, bis-(pentabromophenoxy) ethane, polydibomophenylene oxide, tribromophenylallyl ether, bis-dibromopropyl ether, tetrabromophthalic anhydride, dibromoneopentyl gycol, dibromoethyl dibromocyclohexane, pentabromodiphenyl oxide, tribromostyrene, pentabromochlorocyclohexane, tetrabromoxylene, hexabromocyclododecane, brominated polystyrene, tetradecabromodiphenoxybenzene, trifluoropropene and PVC. Alternatively, the flame retardant may be selected from phosphorus based flame-retardants such as (2,3-dibromopropyl)-phosphate, phosphorus, cyclic phosphates, triaryl phosphate, bis-melaminium pentate, pentaerythritol bicyclic phosphate, dimethyl methyl phosphate, phosphine oxide diol, triphenyl phosphate, tris-(2-chloroethyl) phosphate, phosphate esters such as tricreyl, trixylenyl, isodecyl diphenyl, ethylhexyl diphenyl, phosphate salts of various amines such as ammonium phosphate, trioctyl, tributyl or tris-butoxyethyl phosphate ester. Other flame retardants may include tetraalkyl lead compounds such as tetraethyl lead, iron pentacarbonyl, manganese methyl cyclopentadienyl tricarbonyl, melamine and derivatives such as melamine salts, guanidine, dicyandiamide, ammonium sulphamate, alumina trihydrate, and magnesium hydroxide alumina trihydrate.

The amount of flame retardant will vary depending on factors such as the flame retardant selected and whether solvent is present. However, the amount of flame retardant in the composition may range from greater than 0% to 10% based on the weight of all components in the composition.

Component (K) is a surface modifier. Suitable surface modifiers are exemplified by (k1) an adhesion promoter and (k2) a release agent. Suitable adhesion promoters for component (k1) may comprise a transition metal chelate, a hydrocarbonoxysilane such as an alkoxysilane, a combination of an alkoxysilane and a hydroxy-functional polyorganosiloxane, an aminofunctional silane, or a combination thereof. Adhesion promoters are known in the art and may comprise silanes having the formula $R^{19}{}_rR^{20}{}_sSi(OR^{21})_{4-(r+s)}$ where each $R^{19}$ is independently a monovalent organic group having at least 3 carbon atoms; $R^{20}$ contains at least one SiC bonded substituent having an adhesion-promoting group, such as amino, epoxy, mercapto or acrylate groups: subscript r has a value ranging from 0 to 2; subscript s is either 1 or 2; and the sum of (r+s) is not greater than 3. Alternatively, the adhesion promoter may comprise a partial condensate of the above silane. Alternatively, the adhesion promoter may comprise a combination of an alkoxysilane and a hydroxy-functional polyorganosiloxane.

Alternatively, the adhesion promoter may comprise an unsaturated or epoxy-functional compound. The adhesion promoter may comprise an unsaturated or epoxy-functional alkoxysilane. For example, the functional alkoxysilane can have the formula $R^{22}{}_tSi(OR^{23})_{(4-t)}$, where subscript t is 1, 2, or 3, alternatively subscript t is 1. Each $R^{22}$ is independently a monovalent organic group with the proviso that at least one $R^{22}$ is an unsaturated organic group or an epoxy-functional organic group. Epoxy-functional organic groups for $R^{22}$ are exemplified by 3-glycidoxypropyl and (epoxycyclohexyl) ethyl. Unsaturated organic groups for $R^{22}$ are exemplified by 3-methacryloyloxypropyl, 3-acryloyloxypropyl, and unsaturated monovalent hydrocarbon groups such as vinyl, allyl, hexenyl, undecylenyl. Each $R^{23}$ is independently a saturated hydrocarbon group of 1 to 4 carbon atoms, alternatively 1 to 2 carbon atoms. $R^{23}$ is exemplified by Me, Et, Pr. and Bu.

Examples of suitable epoxy-functional alkoxysilanes include 3-glycidoxypropyltrimethoxysilane, 3-glycidoxypropyltriethoxysilane, (epoxycyclohexyl)ethyldimethoxysilane, (epoxycyclohexyl)ethyldiethoxysilane and combinations thereof. Examples of suitable unsaturated alkoxysilanes include vinyltrimethoxysilane, allyltrimethoxysilane, allyltriethoxysilane, hexenyltrimethoxysilane, undecylenyltrimethoxysilane, 3-methacryloyloxypropyl trimethoxysilane, 3-methacryloyloxypropyl triethoxysilane, 3-acryloyloxypropyl trimethoxysilane, 3-acryloyloxypropyl triethoxysilane, and combinations thereof.

Alternatively, the adhesion promoter may comprise an epoxy-functional siloxane such as a reaction product of a hydroxy-terminated polyorganosiloxane with an epoxy-functional alkoxysilane, as described above, or a physical blend of the hydroxy-terminated polyorganosiloxane with the epoxy-functional alkoxysilane. The adhesion promoter may comprise a combination of an epoxy-functional alkoxysilane and an epoxy-functional siloxane. For example, the adhesion promoter is exemplified by a mixture of 3-glycidoxypropyltrimethoxysilane and a reaction product of hydroxy-terminated methylvinylsiloxane with 3-glycidoxypropyltrimethoxysilane, or a mixture of 3-glycidoxypropyltrimethoxysilane and a hydroxy-terminated methylvinylsiloxane, or a mixture of 3-glycidoxypropyltrimethoxysilane and a hydroxy-terminated methylvinyl/dimethylsiloxane copolymer.

Alternatively, the adhesion promoter may comprise an aminofunctional silane, such as an aminofunctional alkoxysilane exemplified by $H_2N(CH_2)_2Si(OCH_3)_3$, $H_2N(CH_2)_2Si(OCH_2CH_3)_3$, $H_2N(CH_2)_3Si(OCH_3)_3$, $H_2N(CH_2)_3Si(OCH_2CH_3)_3$, $CH_3NH(CH_2)_3Si(OCH_3)_3$, $CH_3NH(CH_2)_3Si(OCH_2CH_3)_3$, $CH_3NH(CH_2)_5Si(OCH_3)_3$, $CH_3NH(CH_2)_5Si(OCH_2CH_3)_3$, $H_2N(CH_2)_2NH(CH_2)_3Si(OCH_3)_3$, $H_2N(CH_2)_2NH(CH_2)_3Si(OCH_2CH_3)_3$. $CH_3NH(CH_2)_2NH(CH_2)_3Si(OCH_3)_3$, $CH_3NH(CH_2)_2NH(CH_2)_3Si(OCH_2CH_3)_3$, $C_4H_9NH(CH_2)_2NH(CH_2)_3Si(OCH_3)_3$, $C_4H_9NH(CH_2)_2NH(CH_2)_3Si(OCH_2CH_3)_3$, $H_2N(CH_2)_2SiCH_3(OCH_3)_2$, $H_2N(CH_2)_2SiCH_3(OCH_2CH_3)_2$, $H_2N(CH_2)_3SiCH_3(OCH_3)_2$, $H_2N(CH_2)_3SiCH_3(OCH_2CH_3)_2$, $CH_3NH(CH_2)_3SiCH_3(OCH_3)_2$, $CH_3NH(CH_2)_3SiCH_3(OCH_2CH_3)_2$, $CH_3NH(CH_2)_5SiCH_3(OCH_3)_2$, $CH_3NH(CH_2)_5SiCH_3(OCH_2CH_3)_2$, $H_2N(CH_2)_2NH(CH_2)_3SiCH_3(OCH_3)_2$, $H_2N(CH_2)_2NH(CH_2)_3SiCH_3(OCH_2CH_3)_2$, $CH_3NH(CH_2)_2NH(CH_2)_3SiCH_3(OCH_3)_2$, $CH_3NH(CH_2)_2NH(CH_2)_3SiCH_3(OCH_2CH_3)_2$, $C_4H_9NH(CH_2)_2NH(CH_2)_3SiCH_3(OCH_3)_2$, $C_4H_9NH(CH_2)_2NH(CH_2)_3SiCH_3(OCH_2CH_3)_2$, and a combination thereof.

Alternatively, the adhesion promoter may comprise a transition metal chelate. Suitable transition metal chelates include titanates, zirconates such as zirconium acetylacetonate, aluminum chelates such as aluminum acetylacetonate, and combinations thereof. Alternatively, the adhesion promoter may comprise a combination of a transition metal chelate with an alkoxysilane, such as a combination of glycidoxypropyltrimethoxysilane with an aluminum chelate or a zirconium chelate.

Component (k2) is a release agent. Suitable release agents are exemplified by fluorinated compounds, such as fluoro-functional silicones, or fluoro-functional organic compounds.

Alternatively, the surface modifier for component (K) may be used to change the appearance of the surface of a reaction product of the composition. For example, surface modifier may be used to increase gloss of the surface of a reaction product of the composition. Such a surface modifier may comprise a polydiorganosiloxane with alkyl and aryl groups. For example, DOW CORNING® 550 Fluid is a trimethylsiloxy-terminated poly(dimethyl/methylphenyl)siloxane with a viscosity of 125 cSt that is commercially available from Dow Corning Corporation of Midland, Mich., U.S.A.

Alternatively, component (K) may be a natural oil obtained from a plant or animal source, such as linseed oil, tung oil, soybean oil, castor oil, fish oil, hempseed oil, cottonseed oil, oiticica oil, or rapeseed oil.

The exact amount of component (K) depends on various factors including the type of surface modifier selected as component (K) and the end use of the composition and its reaction product. However, component (K), when present, may be added to the composition in an amount ranging from 0.01 to 50 weight parts based on the weight of the composition, alternatively 0.01 to 10 weight parts, and alternatively 0.01 to 5 weight parts. Component (K) may be one adhesion promoter. Alternatively, component (K) may comprise two or more different surface modifiers that differ in at least one of the following properties: structure, viscosity, average molecular weight, polymer units, and sequence.

Chain lengtheners may include difunctional silanes and difunctional siloxanes, which extend the length of polyorganosiloxane chains before crosslinking occurs. Chain lengtheners may be used to reduce the modulus of elongation of the cured product. Chain lengtheners compete in their reactions with aliphatically unsaturated groups and/or silicon bonded hydrogen atoms in other components of the composition, e.g., components (B) and/or component (C), when present. Dimethylhydrogensiloxy-terminated polydimethylsiloxanes having relatively low degrees of polymerization (e.g., DP ranging from 3 to 50) may be used as component (L). Component (L) may be one chain lengthener. Alternatively, component (L) may comprise two or more different chain lengtheners that differ in at least one of the following properties: structure, viscosity, average molecular weight, polymer units, and sequence.

Component (M) is and endblocker comprising an M-unit, i.e., a siloxane unit of formula $R^{24}_3SiO_{1/2}$, where each $R^{24}$ independently represents a monovalent, non-functional, organic group, such as a monovalent hydrocarbon group free of aliphatic unsaturation. Component (M) may comprise polyorganosiloxanes endblocked on one terminal end by a triorganosilyl group, e.g., $(CH_3)_3SiO—$, and on the other end by a silicon-bonded hydrogen atom and/or an aliphatically unsaturated organic group. Component (M) may be a polydiorganosiloxane such as a polydimethylsiloxane. The polydiorganosiloxanes having both silicon bonded hydrogen terminals and triorganosilyl end groups, may have more than 50%, alternatively more than 75%, of the total end groups as silicon bonded hydrogen atoms. The amount of triorganosilyl group in the polydimethylsiloxane may be used to regulate the modulus of a cured product prepared by curing the composition. Without wishing to be bound by theory, it is thought that higher concentrations of triorganosilyl end groups may provide a lower modulus in cured products. Component (M) may be one endblocker. Alternatively, component (M) may comprise two or more different endblockers that differ in at least one of the following properties: structure, viscosity, average molecular weight, polymer units, and sequence.

Component (N) is a flux agent. The composition may comprise 0% to 2% of the flux agent based on the weight of all components in the composition. Molecules containing chemically active functional groups such as carboxylic acid and amines can be used as flux agents. Such flux agents can include aliphatic acids such as succinic acid, abietic acid, oleic acid, and adipic acid; aromatic acids such as benzoic acids; aliphatic amines and their derivatives, such as triethanolamine, hydrochloride salts of amines, and hydrobromide salts of amines. Flux agents are known in the art and are commercially available.

Component (O) is an anti-aging additive. The anti-aging additive may comprise an antioxidant, a UV absorber, a UV stabilizer, a heat stabilizer, or a combination thereof. Suitable antioxidants are known in the art and are commercially available. Suitable antioxidants include phenolic antioxidants and combinations of phenolic antioxidants with stabilizers. Phenolic antioxidants include fully sterically hindered phenols and partially hindered phenols; and sterically hindered amines such as tetramethyl-piperidine derivatives. Suitable phenolic antioxidants include vitamin E and IRGANOX® 1010 from Ciba Specialty Chemicals, U.S.A. IRGANOX® 1010 comprises pentaerythritol tetrakis(3-(3, 5-di-t-butyl-4-hydroxyphenyl)propionate). Examples of UV absorbers include phenol, 2-(2H-benzotriazol-2-yl)-6-dodecyl-4-methyl-, branched and linear (TINUVIN® 571). Examples of UV stabilizers include bis(1,2,2,6,6-pentamethyl-4-piperidyl) sebacate; methyl 1,2,2,6,6-pentamethyl-4-piperidyl/sebacate; and a combination thereof (TINUVIN® 272). These and other TINUVIN® additives, such as TINUVIN® 765 are commercially available from Ciba Specialty Chemicals of Tarrytown, N.Y., U.S.A. Other UV and light stabilizers are commercially available, and are exemplified by LowLite from Chemtura, OnCap from PolyOne, and Light Stabilizer 210 from E. I. du Pont de Nemours and Company of Delaware, U.S.A. Oligomeric (higher molecular weight) stabilizers may alternatively be used, for example, to minimize potential for migration of the stabilizer out of the composition or the cured product thereof. An example of an oligomeric antioxidant stabilizer (specifically, hindered amine light stabilizer (HALS)) is Ciba TINUVIN® 622, which is a dimethylester of butanedioic acid copolymerized with 4-hydroxy-2,2,6,6-tetramethyl-1-piperidine ethanol. Heat stabilizers may include iron oxides and carbon blacks, iron carboxylate salts, cerium hydrate, barium zirconate, cerium and zirconium octoates, and porphyrins.

The amount of component (O) depends on various factors including the specific anti-aging additive selected and the anti-aging benefit desired. However, the amount of component (O) may range from 0 to 5 weight %, alternatively 0.1% to 4%, and alternatively 0.5 to 3 weight %, based on the weight of all components in the composition. Component (O) may be one anti-aging additive. Alternatively, component (O) may comprise two or more different anti-aging additives.

Component (P) is a pigment. For purposes of this application, the term 'pigment' includes any component used to impart color to a reaction product of a composition described herein. The amount of pigment depends on various factors including the type of pigment selected and the desired degree of coloration of the product. For example, the composition may comprise 0 to 20%, alternatively 0.001% to 5%, of a pigment based on the weight of all components in the composition.

Examples of suitable pigments include indigo, titanium dioxide Stan-Tone 50SP01 Green (which is commercially available from PolyOne) and carbon black. Representative, non-limiting examples of carbon black include Shawinigan Acetylene black, which is commercially available from Chevron Phillips Chemical Company LP; SUPERJET® Carbon Black (LB-1011) supplied by Elementis Pigments Inc., of Fairview Heights, Ill. U.S.A.; SR 511 supplied by Sid Richardson Carbon Co, of Akron, Ohio U.S.A.: and N330, N550, N762, N990 (from Degussa Engineered Carbons of Parsippany, N.J., U.S.A.).

Component (Q) is an acid acceptor. Suitable acid acceptors include magnesium oxide, calcium oxide, and combinations thereof. The composition may comprise 0% to 2% of component (Q) based on the weight of the composition.

The composition may optionally further comprise up to 5%, alternatively 1% to 2% based on the weight of the composition of component (R) a rheological additive for modifying rheology of the composition. Rheological additives are known in the art and are commercially available. Examples include polyamides, Polyvest, which is commercially available from Evonk, Disparlon from King Industries, Kevlar Fibre Pulp from Du Pont, Rheospan from Nanocor, and Ircogel from Lubrizol. Other suitable rheological additives include polyamide waxes; hydrogenated castor oil derivatives; and metal soaps such as calcium stearate, aluminum stearate and barium stearate, and combinations thereof.

Alternatively, component (R) may comprise a microcrystalline wax that is a solid at 25° C. (wax). The melting point may be selected such that the wax has a melting point at the low end of the desired application temperature range. Without wishing to be bound by theory, it is thought that component (R) acts as a process aid that improves flow properties of the composition. Without wishing to be bound by theory, it is thought that incorporation of wax may also facilitate incorporation of fillers, compounding and de-airing (during production of the composition), and mixing (static or dynamic mixing during application of parts of a multiple part composition). It is thought that the wax, when molten, serves as a process aid, substantially easing the incorporation of filler in the composition during compounding, the compounding process itself, as well as in during a de-airing step, if used. The wax, with a melt temperature below 100° C., may facilitate mixing of the parts of a multiple part composition before application, even in a simple static mixer.

Waxes suitable for use as component (R) may be non-polar hydrocarbons. The waxes may have branched structures, cyclic structures, or combinations thereof. For example, petroleum microcrystalline waxes are available from Strahl & Pitsch, Inc., of West Babylon, N.Y., U.S.A. and include SP 96 (melting point ranging from 62° C. to 69° C.), SP 18 (melting point ranging from 73° C. to 80° C.), SP 19 (melting point ranging from 76° C. to 83° C.), SP 26 (melting point ranging from 76° C. to 83° C.), SP 60 (melting point ranging from 79° C. to 85° C.), SP 617 (melting point ranging from 88° C. to 93° C.), SP 89 (melting point ranging from 90° C. to 95° C.), and SP 624 (melting point ranging from 90° C. to 95° C.). Other petroleum microcrystalline waxes include waxes marketed under the trademark Multiwax® by Crompton Corporation of Petrolia, Pa., U.S.A. These waxes include 180-W, which comprises saturated branched and cyclic non-polar hydrocarbons and has melting point ranging from 79° C. to 87° C.; Multiwax® W-445, which comprises saturated branched and cyclic non-polar hydrocarbons, and has melting point ranging from 76° C. to 83° C.; and Multiwax® W-835, which comprises saturated branched and cyclic non-polar hydrocarbons, and has melting point ranging from 73° C. to 80° C.

The amount of component (R) depends on various factors including the specific rheological additive selected and the selections of the other components of the composition. However, the amount of component (R) may range from 0 parts to 20 parts, alternatively 1 part to 15 parts, and alternatively 1 part to 5 parts based on the weight of all components in the composition. Component (R) may be one rheological additive. Alternatively, component (R) may comprise two or more different rheological additives.

A vehicle may be used in the composition. The vehicle may facilitate flow of the composition and introduction of certain components, such as silicone resin. Vehicles used herein are those that help fluidize the components of the composition but essentially do not react with the components. The vehicle may be selected based on solubility the components in the composition and volatility. The solubility refers to the vehicle being sufficient to dissolve and/or disperse components of the composition. Volatility refers to vapor pressure of the vehicle. If the vehicle is too volatile (having too high vapor pressure) bubbles may form in the composition during hydrosilylation reaction, and the bubbles may cause cracks or otherwise weaken or detrimentally affect properties of the reaction product. However, if the vehicle is not volatile enough (too low vapor pressure) the vehicle may remain as a plasticizer in the reaction product of the composition.

Suitable vehicles include polyorganosiloxanes with suitable vapor pressures, such as hexamethyldisiloxane, octamethyltrisiloxane, hexamethylcyclotrisiloxane and other low molecular weight polyorganosiloxanes, such as 0.5 to 1.5 cSt Dow Corning® 200 Fluids and Dow Corning® OS FLUIDS, which are commercially available from Dow Corning Corporation of Midland, Mich., U.S.A.

Alternatively, the vehicle may comprise an organic solvent. The organic solvent can be an alcohol such as methanol, ethanol, isopropanol, butanol, or n-propanol; a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride; chloroform; dimethyl sulfoxide; dimethyl formamide, acetonitrile; tetrahydrofuran; white spirits; mineral spirits; naphtha; n-methyl pyrrolidone; or a combination thereof.

The amount of vehicle will depend on various factors including the type of vehicle selected and the amount and type of other components selected for the composition. However, the amount of vehicle may range from 1% to 99%, alternatively 2% to 50%, based on the weight of all components in the composition. Component (S) can be added during preparation of the composition, for example, to aid mixing and delivery. All or a portion of component (S) may optionally be removed after the composition is prepared.

Component (T) is a surfactant. Suitable surfactants include silicone polyethers, ethylene oxide polymers, propylene oxide polymers, copolymers of ethylene oxide and propylene oxide, other non-ionic surfactants, and combinations thereof. The composition may comprise 0% to 0.05% of the surfactant based on the weight of all components in the composition.

Component (U) is a corrosion inhibitor. Examples of suitable corrosion inhibitors include benzotriazole, mercaptabenzotriazole and commercially available corrosion inhibitors such as 2,5-dimercapto-1,3,4-thiadiazole derivative (CUVAN® 826) and alkylthiadiazole (CUVAN® 484) from R. T. Vanderbilt of Norwalk, Conn., U.S.A. When present, the amount of component (U) may range from 0.05% to 0.5% based on the weight of the composition.

When selecting components for the composition described above, there may be overlap between types of components because certain components described herein may have more than one function. For example, certain alkoxysilanes may be useful as filler treating agents and as adhesion promoters, and certain plasticizers such as fatty acid esters may also be useful as filler treating agents. Certain particulates may be useful as fillers and as pigments, and even as flame retardants, e.g., carbon black. When adding additional components to the composition, the additional components are distinct from one another.

The composition can be prepared by a method comprising combining all components by any convenient means such as mixing at ambient or elevated temperature. Component (I), when present, may be added before component (A), for example, when the composition will be prepared at elevated temperature and/or the composition will be prepared as a one part composition.

When component (G) is present, the composition may optionally be prepared by surface treating a particulate component (e.g., filler and/or spacer, if present) with component (G), and thereafter mixing the product thereof with the other components of the composition.

Alternatively, the composition may be prepared as a multiple part composition, for example, when component (I) is absent, or when the composition will be stored for a long period of time before use. In the multiple part composition, component (A) is stored in a separate part from any component having a silicon bonded hydrogen atom, for example component (C), and the parts are combined shortly before use of the composition. For example, a two part composition may be prepared by combining components comprising (B), (A), (F), and optionally one or more other additional components described above to form a base by any convenient means such as mixing. A curing agent may be prepared by combining components comprising (B), (C), and optionally one or more other additional components described above by any convenient means such as mixing. The components may be combined at ambient or elevated temperature. When a two part composition is used, the weight ratio of amounts of base to curing agent may range from 1:1 to 10:1. The composition will react via hydrosilylation reaction to form a reaction product. The reaction product may have various forms, such as a silane, a gum, a gel, a rubber, or a resin.

EXAMPLES

These examples are intended to illustrate some embodiments of the invention and should not be interpreted as limiting the scope of the invention set forth in the claims. The following components were used in the examples.

The bolded headers of chemical structures, followed by a designation of a number and letter in parentheses, refers in shorthand nature to the chemical structure illustrated and described above for the ligand components and reaction products described above. More specifically, the abbreviations for the ligand components described below follow the general formula (5):$R1_PX_NR^2_NZ$, wherein $R^1$, X and $R^2$ are as described above in general formula (1) and wherein the superscript Z represents the substitution present on the pyridyl group (Y as described in general formula 1). When $R^1$ is an unsubstituted phenyl group, no superscript is provided in the general formula. Also, when Z is a hydrogen atom, and hence Y is an unsubstituted pyridyl group, no Z superscript is presented in formula (5).

By way of an example, the formula: $P^{Ar}N^{Me}N$ (1A), which is described immediately below, refers to the ligand component of Formula (1A) described above, wherein the superscript Ar represents the substituted or unsubstituted arylene group corresponding to X in general formula (1), and wherein the superscript Me represents a methyl group corresponding to $R^2$ in general formula (1), and wherein Y is an unsubstituted pyridyl group (i.e., wherein no Z superscript is present). By way of a second example, $P^{Pr}N^HN^{Ph}$ (1D), also described below, refers to the ligand component of Formula (1D) described above, wherein the superscript Pr represents the propylene group corresponding to X in general formula (1), and wherein the superscript H represents a hydrogen atom corresponding to $R^2$ in general formula (1), and superscript Ph represents a substituted or unsubstituted phenyl group coupled to the carbon atom in the ring structure adjacent to the nitrogen atom (i.e., wherein Y is a 6-phenylpyridyl group). In each of these three formulas, because $R^1$ is an unsubstituted phenyl group, this species disappears from the formulas.

Example 1: Preparation and Characterization of PNN Ligands of Formulas (1A)-(1I) Preparation and Characterization of $P^{Ar}N^{Me}N$ (1A)

2-acetylpyridine (998 mg, 8.23 mmol) and o-diphenylphosphinoaniline (906 mg, 3.98 mmol) was combined with 20 mL of toluene and 4 Å molecular sieves in a screw cap round bottom flask. 1 drop of trifluoroacetic acid was added to the mixture and the flask was sealed. The mixture was heated in a 115° C. oil bath for 48 hours. The mixture was then cooled and filtered. Volatiles were removed under reduced pressure. The resulting yellow oil was dissolved in a minimal amount of $Et_2O$ and recrystallised in pentane under −10° C. to obtain 102 mg (6.5% yield) of $P^{Ar}N^{Me}N$ as white powder.

$^{31}P$ NMR ($CDCl_3$, 202.4 MHz): δ=−13.9 (1P, s)

$^1H$ NMR ($CDCl_3$, 500 MHz): δ=8.54 (1H, ddd, J=4.7, 1.7, 0.7 Hz); 8.03 (1H, ddd.J=8.0, 0.7, 0.7 Hz); 7.71 (1H, ddd, J=7.8, 7.7, 1.8 Hz); 7.37-7.26 (12H, m); 7.04 (1H, dddd, J=7.7, 7.4, 1.0, 0.7 Hz); 6.89 (1H, ddd, J=7.6, 4.4, 1.3 Hz); 6.74 (1H, ddd, J=7.7, 4.5, 0.9 Hz); 1.97 (3H, d, J=0.7 Hz).

Preparation and Characterization of $P^{Ar}N^{pH}N$ (1B)

Benzoyl pyridine (2.17 g, 11.8 mmol), o-diphenylphosphinoaniline (1.80 g, 7.90 mmol) and p-toluenesulfonicacid monohydrate (75 mg, 0.39 mmol) was combined in 50 mL of toluene in a schlenk flask. The flask was fitted with a dean-stark trap and the mixture was heated to reflux for 36 hours. The solution was then cooled and washed with $NaHCO_3$(aq). The organic layer was dried with $MgSO_4$ and volatiles were removed under reduced pressure. The resulting yellow oil was dissolved in a minimal amount of DCM and recrystallised from $Et_2O$ under −10° C. to yield $P^{Ar}N^{-Ph}N$ (1.87 g, 4.43 mmol, 53% yield) as yellow crystals.

$^{31}P$ NMR ($CDCl_3$, 202.4 MHz): δ=−13.6 (1P, s, Isomer 1); −13.7 (1P, s. Isomer 1).

$^1H$ NMR ($CDCl_3$, 500 MHz): δ=8.61 (2H, dd, J=37.0, 4.6 Hz); 8.05 (1H, d, J=7.7 Hz); 7.72 (1H, td J=7.6, 1.3 Hz); 7.60 (2H, d, J=7.8 Hz); 7.45-7.15 (10H, m) 7.05-6.85 (4H, m); 6.44 (2H, m); 6.29 (1H, d, J=7.8 Hz).

Preparation and Characterization of Other Liquid Ligand Components (1C)-(1E)

$Ph_2P(CH_2)_3NH_2$ and 1 equivalent of the corresponding pyridine were combined in THF and stirred in room temperature. After 1 hour, volatiles were removed under reduced pressure to afford the ligand components (1C)-(1E) below in greater than a 99% yield.

Characterization of $P^{Pr}N^HN^H$ (1C)

$^{31}P$ NMR ($CDCl_3$, 202.4 MHz) δ−15.3 (1P, s)

$^1H$ NMR ($CDCl_3$, 500 MHz) δ 8.66-8.62 (m, 1H, pyH), 8.37 (s, 1H, N=CH), 7.97 (d, J=7.9, 1H, pyH), 7.74 (td, J=7.7, 1.8 Hz, 1H, pyH), 7.46-7.28 (m, 11H), 3.76 (t, J=6.8 Hz, 2H, CH), 2.18-2.10 (m, 2H, CH), 1.92-1.83 (m, 2H, CH).

Characterization of P$^{Pr}$N$^H$N$^{pH}$ (1D)

$^{31}$P NMR (CDCl$_3$, 202.4 MHz) δ−18.9 (1P, s)
$^1$H NMR (CDCl$_3$, 500 MHz) δ 8.48 (s, 1H, N=CH), 8.04 (d, J=7.8 Hz, 2H), 7.96 (d, J=7.6 Hz, 1H), 7.80 (t, J=7.7 Hz, 1H), 7.75 (d, J=7.8 Hz, 1H), 7.56-7.28 (m, 13H), 3.79 (t, J=6.8 Hz, 2H, CH), 2.19-2.13 (m, 2H, CH), 1.91 (m, 2H, CH).

Characterization of P$^{Pr}$N$^H$N$^{Me}$ (1E)

$^{31}$P NMR (CDCl$_3$, 202.4 MHz) δ−15.6 (1P, s)
$^1$H NMR (CD$_2$Cl$_2$, 500 MHz) δ 8.32 (1H, s, N=CH), 7.74 (d, J=7.7 Hz, 1H, pyH), 7.57 (d, J=7.7 Hz, 1H, pyH), 7.39 (td, J=7.4, 1.9 Hz, 4H, ArH), 7.27 (m, 6H, ArH), 7.12 (d, J=7.7 Hz, 1H), 3.71 (td, J=6.7, 0.8 Hz, 2H, CH), 2.55 (s, 3H, CH$_3$), 2.10 (m, 2H CH), 1.84 (m, 2H, CH)

Preparation and Characterization of P$^{Pr}$N$^{pH}$N (1F)

A mixture of Ph$_2$P(CH$_2$)$_3$NH$_2$ (1.40 g, 6.12 mmol), benzoylpyridine (1.12 g, 6.12 mmol) and p-toluenesulfonic acid monohydrate (52 mg, 0.306 mmol) was dissolved in toluene (50 mL) in a schlenk flask. The flask was equipped with a Dean-Stark trap and the mixture was heated to reflux for 18 hours. The solution was then washed with saturated NaHCO$_3$(aq) and dried with anhydrous MgSO$_4$. Volatiles were removed under reduced pressure to yield the desired compound as a yellow oil (2.324 g, 93%).

$^{31}$P NMR (CDCl$_3$, 202.4 MHz) δ−15.15 (1P, s, isomer A), 15.19 (1P, s, isomer B)
$^1$H NMR (CDCl$_3$, 500 MHz) δ 8.72-8.69 (m, 1H, isomer A), 8.49-8.45 (m, 1H, isomer B), 8.16 (dt, J=8.0, 1.1 Hz, 2H, isomer A), 7.80-7.73 (m, 4H, isomer A+B), 7.56-7.24 (m, 24H, isomer A+B), 7.17 (dt, J=7.7, 1.2 Hz, 2H, isomer A+B), 7.14-7.11 (m, 4H, isomer A+B), δ 3.49 (t, J=6.8 Hz, 2H, isomer B), 3.41 (t, J=6.7 Hz, 2H, isomer A), 2.17-2.04 (m, 4H, isomer A+B), 1.87-1.69 (m, 4H, isomer A+B).

Preparation of P$^{Ar}$N$^H$N (1G)

A direct synthesis of P$^{Ar}$N$^H$N can be synthesized by templating directly on a metal to form a stable complex (see synthesis of formula (2G) below for details).

Preparation and Characterization of CyP$^{Pr}$N$^H$N (1H)

As described above to a procedure similar to 1C-1E, Cy$_2$P(CH$_2$)$_3$NH$_2$ and 1 equivalent of the 2-pyridinecarboxaldehyde were combined in THF and stirred in room temperature. After 1 hour, volatiles were removed under reduced pressure to afford the ligand (1H) in greater than 99% yield.

$^{31}$P NMR (CDCl$_3$, 202.4 MHz) δ−5.3 (1P, s)
$^1$H NMR (C6D6, 500 MHz) δ 8.62 (m, 1H, N=CH), 8.53-8.45 (m, 1H, pyH), 8.20 (m, 1H, pyH), 7.07-7.01 (m, 1H, ArH), 6.61 (m, 1H, pyH), 3.62 (td, J=6.8, 1.5 Hz, 2H), 2.04-1.01 (m, 26H, CH, cyH)

Preparation and Characterization of $^i$PrP$^{Pr}$N$^H$N (1I)

As described above to a procedure similar to 1C-1E, $^i$Pr$_2$P(CH$_2$)$_3$NH$_2$ and 1 equivalent of the 2-pyridinecarboxaldehyde were combined in THF and stirred in room temperature. After 1 hour, volatiles were removed under reduced pressure to afford the ligand (1I) in greater than 99% yield.

$^1$H NMR (500 MHz, Benzene-d6): δ 8.59 (s, 1H, C=NH), 8.52-8.42 (m, 1H, py-H), 8.18 (m, 1H, pyH), 7.04 (td, J=7.6, 1.8 Hz, 1H, pyH), 6.61 (ddd, J=7.4, 4.8, 1.3 Hz, 1H, pyH), 3.57 (td, J=6.7, 1.5 Hz, 2H, CH$_2$), 1.97-1.86 (m, 2H, CH$_2$), 1.59-1.52 (m, 2H, methine-H), 1.39-1.35 (m, 2H, CH$_2$), 1.05-0.97 (m, 12H, CH$_3$).

Example 2: Preparation of Reaction Products

Preparation and Characterization of Co(P$^{Ar}$N$^{Me}$N)Cl$_2$ (2A)

Equimolar of CoCl$_2$ and P$^{Ar}$N$^{Me}$N were combined and dissolved in THF. After about 1 minute, a dark red-brown precipitate started to form. After stirring for 3 hours, this mixture was filtered through a frit to obtain red-brown powders that is the product. To further purify the powders, it was dissolved in a minimum amount of CH$_2$Cl$_2$ and precipitated with pentane.

$^1$H NMR (500 MHz, CD$_2$Cl$_2$) δ 170.04, 69.05, 58.86, 22.28, 17.86, 12.26, 9.22, 4.64, −7.60, −11.72, −12.81.

Preparation and Characterization of Fe(P$^{Ar}$N$^{pH}$N)Br$_2$ (2B)

Iron dibromide (80 mg, 0.37 mmol) was stirred in THF (3 mL). A solution of PN$^{Ph}$N (156 mg, 0.37 mmol) in THF was slowly added, leading to a color change from yellow to blue/green. The mixture was stirred for 3 hours, leading to a precipitation of some blue/green solid. Pentane (10 mL) was then added while stirring leading to further precipitation of blue/green solid. This solid was collected by filtration, washed with pentane (2×5 mL) and dried to yield Fe(P$^{Ar}$N-$^{Ph}$N)Br$_2$, (2A) (210 mg, 0.33 mmol, 89% yield) as a blue green solid.

$^1$H NMR (CD$_2$Cl$_2$, 500 MHz): δ 76.44, 67.99, 17.99, 14.65, 14.06, 13.42, 7.79, 5.67, −1.70, −3.84.

Preparation and Characterization of Co(P$^{Ar}$N$^{pH}$N)Cl$_2$ (2C)

Equimolar of CoCl$_2$ and P$^{Ar}$N$^{Ph}$N were combined and dissolved in THF. After about 1 minute, a dark red-brown precipitate started to form. After stirring for 3 hours, this mixture was filtered through a frit to obtain red-brown powders that is the product. To further purify the powders, it was dissolved in a minimum amount of CH$_2$Cl$_2$ and precipitated with pentane.

$^1$H NMR (500 MHz, CD$_2$Cl$_2$) δ 171.00, 66.32, 58.90, 23.35, 17.29, 11.95, 10.48, 10.01, 6.65, −7.21, −13.08.

Preparation and Characterization of Co(P$^{Pr}$N$^{pH}$N)Cl$_2$ (2D)

Equimolar of CoCl$_2$ and P$^{Pr}$N$^{Ph}$N were combined and dissolved in THF. After about 1 minute, a dark red-brown precipitate started to form. After stirring for 3 hours, this mixture was filtered through a frit to obtain red-brown powders that is the product. To further purify the powders, the product was dissolved in a minimum amount of CH$_2$Cl$_2$ and precipitated with pentane.

$^1$H NMR (500 MHz, CD$_2$Cl$_2$) δ 200.95, 145.47, 109.16, 66.01, 62.61, 21.82, 13.82, 11.88, 10.12, 3.88, −0.37. −4.57, −15.03.

Preparation of Co(P$^E$N$^H$N)Cl (2E)

CoCl$_2$ (81.5 mg, 0.62 mmol) was dissolved in THF and stirred at room temperature for 1 hour. In a separate flask, sodium spheres (17.4 mg, 0.76 mmol) and P$^{Et}$N$^H$N (200 mg, 0.63 mmol) were combined in THF and stirred to give a dark red mixture that is [Na]P$^{Et}$N$^H$N. After 1 hour, the [Na]P$^{Et}$N$^H$N solution was filtered through celite into the stirred CoCl$_2$ solution to give a dark purplish-brown mixture. After 2 hours, this mixture was filtered and solvents were removed under reduced pressure. The resulting purplish-brown solids were re-dissolved in a minimal amount of THF and added pentane. The mixture was kept at approximately—35° C. for 18 hours, filtered, washed with diethyl ether to obtain the desired product as purple-brown micro-crystals (189 mg, 72% yield).

$^1$H NMR (500 MHz, C$_6$D$_6$) δ 9.40 (d, J=5.6 Hz, 1H), 7.92 (m, 2H), 7.80 (m, 2H), 7.58-6.50 (m, 5.54 (s, 1H), 2.18-2.04 (m, 1H), 1.85-1.74 (m, 2H), 1.57-1.46 (m, 1H)

$^{31}$P NMR. (202.4 MHz, C$_6$D$_6$) δ 40 (1P).

Preparation and Characterization of Co(P$^{Ar}$N$^H$N)Cl$_2$ (2F)

CoCl$_2$ (47 mg, 0.36 mmol) and o-diphenylphosphinoaniline (102 mg, 0.37 mmol) were combined and stirred in THF (5 mL) for 30 minutes. After this time, pyridine carboxaldehyde (43 mg, 0.40 mmol) in THF (2 mL) was added dropwise to the stirred solution, resulting in the formation of a purple-brown precipitate. The solution was stirred for two hours before filtering with the solid being collected, washed with pentane (2×5 ml) and dried to yield Co(P$^{Ar}$N$^H$N)C$_2$ (154 mg, 0.31 mmol, 86% yield).

$^1$H NMR (500 MHz, CD$_2$Cl$_2$) δ 62.71, 49.72, 33.20, 26.87, 11.67, −2.68, −10.11, −15.53.

Preparation and Characterization of Co($^i$PrP$^{Pr}$N$^H$N) Cl$_2$ (2G)

$^i$Pr$_2$P(CH$_2$)$_3$NH$_2$ (192 mg, 1.1 mmol)) and 2-pyridinecarboxaldehyde (120 mg, 1.1 mmol) were mixed in THF and stirred at room temperature for 1 hour, followed by addition of a THF solution containing CoCl$_2$ (142 mg, 1.1 mmol). The resulting red mixture was stirred at room temperature for an additional 4 hours, followed by filtration using a medium frit. The collected red powder was recrystallized using DCM/pentane to yield dark red crystals (338 mg, 78%).

$^1$H NMR (500 MHz, CD$_2$Cl$_2$): δ 194.12, 124.47, 100.85, 98.76, 62.50, 47.83, 1.84, 0.54, −2.78, −7.63.

Preparation and Characterization of Co(P$^{Et}$N$^H$N)Me (2H)

Co(P$^{Et}$N$^H$N)Cl (100 mg, 0.24 mmol) was added Et$_2$O (5 mL) and cooled to −35° C. A 1.6M MeLi solution in Et$_2$O (0.18 mL, 0.28 mmol) was added to this solution. After stirring in room temperature for 24 hours, the solution was filtered and volatiles removed under reduced pressure to give and oily purplish-brown residue. The residue was dissolved in a minimum amount of THF, layered with pentane and stored in approximately 35° C. for 18 hours. The solution was then filtered to give a dark powder. Single crystals suitable for X-ray diffraction were also obtained this way.

$^1$H NMR (500 MHz, C$_6$D$_6$) δ 8.27 (d, J=5.6 Hz, 1H), 7.47-7.52 (m, 2H), 7.34-7.27 (m, 2H), 7.25-6.93 (m, 6H), 6.73-6.68 (m, 1H), 6.66-6.63 (m, 1H), 6.48 (d, J=8.1 Hz, 1H), 4.31 (s, 1H), 2.48-2.33 (m, 1H), 1.97 (m, 1H), 1.85-1.70 (m, 2H), −0.28 (d, J=7.1 Hz, 3H).

Example 3: Evaluation of Activated Reaction Products Based on P$^{Ar}$N$^{Ph}$N (1B) Combined with Various Metal Precursors for their Ability to Catalyze a Hydrosilylation Reaction In a first example, various metal precursors were combined with P$^{Ar}$N$^{Ph}$N (Formula 1B) to form a reaction product, which was then activated using the reducing agent NaEt$_3$BH to form an activated reaction product. The various activated reaction products were evaluated for their ability to catalyze a hydrosilylation reaction of 1:1 molar ratios of vinylmethyldi(trimethoxy)siloxane (vinyl-di-siloxane) and 1,1,1,3,5,5,5-Heptamethyltrisiloxane (HMTS). The reaction proceeds according to the following general reaction scheme, with four potential products A, A', B and C as shown below:

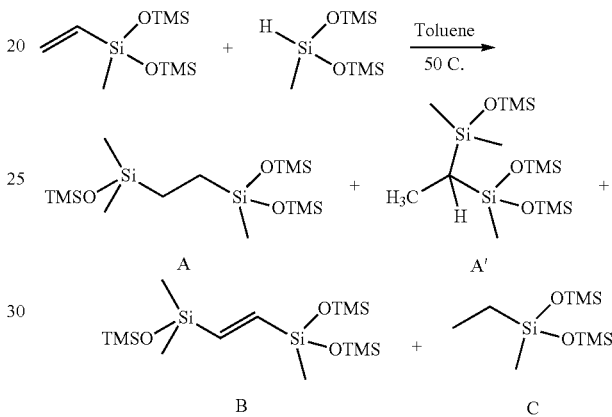

(1) A scintillation vial was charged with 0.4 mL of FeBr$_2$ (0.025M in THF) and 0.4 mL of P$^{Ar}$N$^{Ph}$N (0.025M in THF) and the reaction mixture was stirred at 250 RPM at 23 degrees Celsius for 12 hours. The solvent was removed in vacuo and was replaced with toluene (1.0 mL). Next, 2 equivalents of NaBEt$_3$H (200 µL, 0.1M) were introduced, vigorously agitated and stirred for 5 minutes at 23 degrees Celsius. A mixture of VPMS (vinylpentamethyl-di-siloxane)(1.744 gm; 2.5 mmol) and HMTS(heptamethyl-tri-siloxane)(2.224 gm; 2.5 mmol) was added to the vial containing activated reaction product and was stirred at 50 degrees Celsius. The reaction mixture was monitored at regular intervals to evaluate the progress of the reaction and was analyzed to determine the relative amount of products formation using spectroscopic techniques. A small amount of reaction mixture (50 µL) was dissolved with CDCl$_3$ and was analyzed by 1H NMR spectroscopy and identity confirmed by GC-MS as well. The conversion and products selectivity are summarized in Table 1.

(2) A scintillation vial was charged with 2.0 mL of CoI$_2$ (0.005M in THF) and 0.4 mL of P$^{Ar}$N$^{Ph}$N (0.025M in THF) and the reaction mixture was stirred at 250 RPM at 23 degrees Celsius for 12 hours. The solvent was removed in vacuo and was replaced with toluene (1.0 mL). Next, 2 equivalent of NaBEt$_3$H (200 µL, 0.1M) was introduced, vigorously agitated and stirred for 5 minutes at 23 degrees Celsius. A mixture of VPMS (vinylpentamethyl-di-siloxane)(1.744 gm; 2.5 mmol) and HMTS(heptamethyl-tri-siloxane)(2.224 gm; 2.5 mmol) was added to the vial containing activated reaction product and was stirred at 50 degrees Celsius.

The reaction mixture was monitored at regular intervals to evaluate the progress of the reaction and was analyzed to determine the relative amount of products formation using spectroscopic techniques. A small amount of reaction mixture (50 uL) was dissolved with CDCl₃ and was analyzed by 1H NMR spectroscopy and identity confirmed by GC-MS as well. The conversion and products selectivity are summarized in Table 1.

(3) A scintillation vial was charged with 2.0 mL of NiBr₂(DME) (0.005M in THF) and 0.4 mL of $P^{Ar}N^{Ph}N$ (0.025M in THF) and the reaction mixture was stirred at 250 RPM at 23 degrees Celsius for 12 hours. The solvent was removed in vacuo and was replaced with toluene (1.0 mL). Next, 2 equivalent of NaBEt₃H (200 µL, 0.1M) was introduced, vigorously agitated and stirred for 5 minutes at 23 degrees Celsius. A mixture of VPMS(vinylpentamethyl-di-siloxane)(1.744 gm; 2.5 mmol) and HMTS(heptamethyl-tri-siloxane)(2.224 gm; 2.5 mmol) was added to the vial containing activated reaction product and was stirred at 50 degrees Celsius. The reaction mixture was monitored at regular intervals to evaluate the progress of the reaction and was analyzed to determine the relative amount of products formation using spectroscopic techniques. A small amount of reaction mixture (50 µL) was dissolved with CDCl₃ and was analyzed by 1H NMR spectroscopy and identity confirmed by GC-MS as well. The conversion and products selectivity are summarized in Table 1.

TABLE 1

| Metal Precursor | Reducing Reagent | Rxn Time | Conversion (%) | Selectivity (%) | | | |
|---|---|---|---|---|---|---|---|
| | | | | A | A' | B | C |
| FeBr₂ | NaEt₃BH | 2 h | 10 | 35 | 9 | 22 | 35 |
| FeBr₂ | NaEt₃BH | 16 h | 53 | 28 | 12 | 24 | 35 |
| CoI₂ | NaEt₃BH | 2 h | 21 | 0 | 0 | 50 | 50 |
| CoI₂ | NaEt₃BH | 16 h | 99 | 0 | 0 | 47 | 53 |
| NiBr₂ | NaEt₃BH | 2 h | 0 | 0 | 0 | 0 | 0 |
| NiBr₂ | NaEt₃BH | 16 h | 0 | 0 | 0 | 0 | 0 |

In a second example, these same activated reaction products as described above, were evaluated for their ability to catalyze a hydrosilylation reaction of 1:1 molar ratios of vinylmethyldi(trimethoxy)siloxane (0.436 gm; 2.5 mmol) and phenylsilane (PhSiH₃)(0.27 gm; 2.5 mmol). In this second example, the reaction proceeds according to the following general reaction scheme, with four potential products A, A', B and C as shown below, and the resultant products conversion and selectivity are summarized in Table 2:

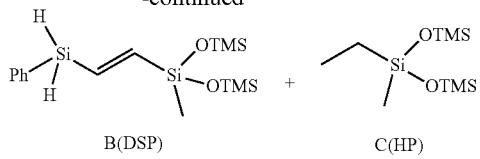

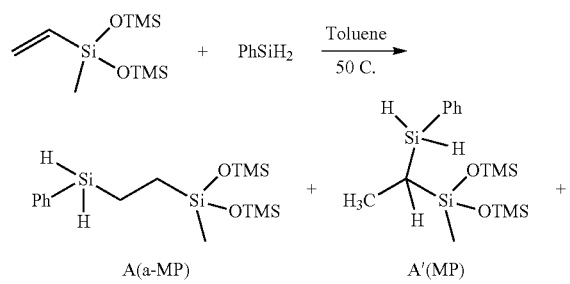

TABLE 2

| Metal Precursor | Reducing Reagent | Rxn Time | Conversion (%) | Selectivity (%) | | | |
|---|---|---|---|---|---|---|---|
| | | | | A | A' | B | C |
| FeBr₂ | NaEt₃BH | 2 h | >99 | >99 | 0 | 0 | 0 |
| FeBr₂ | NaEt₃BH | 16 h | >99 | >99 | 0 | 0 | 0 |
| CoI₂ | NaEt₃BH | 2 h | >99 | 7 | 93 | 0 | 0 |
| CoI₂ | NaEt₃BH | 16 h | >99 | 7 | 93 | 0 | 0 |
| NiBr₂ | NaEt₃BH | 2 h | 5 | 86 | 14 | 0 | 0 |
| NiBr₂ | NaEt₃BH | 16 h | 16 | 87 | 13 | 0 | 0 |

As Tables 1 and 2 confirm, samples utilizing iron (II) bromide as the metal precursor in combination with the ligand component $P^{Ar}N^{Ph}N$ (Formula 1B) achieved higher selectivity for the desired reaction product A in both Tables 1 and 2.

Example 4: Evaluation of Activated Reaction Products for their Ability to Catalyze a Hydrosilylation Reaction In Example 4, ligand components of formulas (1B), (1E), and (1H) of the present invention were combined with certain metal precursors and activated with certain ionic activators to form activated reaction products. The activated reaction products were then evaluated for their ability to catalyze hydrosilyation reactions of 1-octene with various silanes (HMTS, diphenylsilane, or triethylsilane).

Preparation of Activated Reaction Products:

Activated reaction products $Fe(P^{Et}N^HN)(CH_2SiMe_3)_2$, $Fe(P^{Ar}N^{Ph}N)(CH_2SiMe_3)_2$ and $Fe(P^{Et}N^HN)(CH_2SiMe_3)_2$ were prepared according to one of the following formulas and used in Examples A-I below:

Example A

In a nitrogen-filled drybox, a scintillation vial was charged with 141 mg (1.26 mmol) of 1-octene and 1.26 mmol of silane (232 mg, diphenylsilane). 15 mg (0.027 mmol, 2.2% loading) of $Fe(P^{Et}N^HN)(CH_2SiMe_3)_2$ was then added and the reaction was stirred for 2 hours at 50° C. The reaction was quenched by exposure to air and the product mixture was analysed by NMR spectroscopy. Olefin Conversion>95%, AMP (Antimarkovnikov product): 90%, 10 (Internal Olefins from isomerization): 8%.

Examples B and C

In a nitrogen-filled drybox, a J Young NMR tube was charged with 139 mg (1.24 mmol) of 1-octene and 1.24 mmol of silane (229 mg, diphenylsilane). 6.8 mg (0.012 mmol, 1.0% loading) of the complex Fe(P$^{Et}$N$^H$N)(CH$_2$SiMe$_3$)$_2$ and 0.2 mL of C$_6$D$_6$ was then added and the reaction was stirred at room temperature. The reaction mixture was analysed by NMR spectroscopy. At 5 hrs AMP: 42% (Example B), at 50 hours AMP: 70% (Example C).

Example D

In a nitrogen-filled drybox, a scintillation vial was charged with 140 mg (1.25 mmol) of 1-octene and 1.25 mmol of silane (275 mg, HMTS). 6.8 mg (0.012 mmol, 1.0% loading) of the complex Fe(P$^{Et}$N$^H$N)(CH$_2$SiMe$_3$)$_2$ was then added and the reaction was stirred for 2 hours at 50° C. The reaction was quenched by exposure to air and the product mixture was analysed by NMR spectroscopy. Olefin Conversion=>95%, IO: >95%.

Example E

In a nitrogen-filled drybox, a scintillation vial was charged with 139 mg (1.24 mmol) of 1-octene and 1.24 mmol of silane (143 mg, triethylsilane). 6.8 mg (0.012 mmol, 1.0% loading) of the complex Fe(P$^{Et}$N$^H$N)(CH$_2$SiMe$_3$)$_2$ was then added and the reaction was stirred for 2 hours at 50° C. The reaction was quenched by exposure to air and the product mixture was analysed by NMR spectroscopy. Olefin Conversion=>95%, IO: >95%.

Example F

In a nitrogen-filled drybox, a scintillation vial was charged with 137 mg (1.22 mmol) of 1-octene and 1.29 mmol of silane (238 mg, diphenylsilane). 1.5 mg (0.0032 mmol, 0.3% loading) of the complex Co(P$^{Et}$N$^H$N)(CH$_2$SiMe$_3$)$_n$ was then added and the reaction was stirred overnight at 25° C. The reaction was quenched by exposure to air and the product mixture was analysed by NMR spectroscopy. Olefin Conversion>95%, AMP: 44%, MP (Markovnikov product): 56%.

Example G

In a nitrogen-filled drybox, a scintillation vial was charged with 139 mg (1.24 mmol) of 1-octene and 1.24 mmol of silane (275 mg, HMTS). 4.2 mg (0.0090 mmol, 0.7% loading) of the complex Co(P$^{Et}$N$^H$N)(CH$_2$SiMe$_3$)$_n$ was then added and the reaction was stirred overnight at 25° C. The reaction was quenched by exposure to air and the product mixture was analysed by NMR spectroscopy. Olefin Conversion>95%, IO: >95%.

Example H

In a nitrogen-filled drybox, a scintillation vial was charged with 150 mg (1.24 mmol) of 1-octene and 1.24 mmol of silane (276 mg, HMTS). 6.3 mg (0.010 mmol, 0.8% loading) of the complex Co(P$^{Et}$N$^H$N)I$_2$ was then added along with 0.075 mmol of NaBEt$_3$H as a toluene solution, and the reaction was stirred for 3 hours at 25° C. The reaction was quenched by exposure to air and the product mixture was analysed by NMR spectroscopy. Olefin Conversion=>95%, IO: >95%.

Example I

In a nitrogen-filled drybox, a scintillation vial was charged with 520 mg of a 1:1 mixture of 1-octene: HMTS (1.50 mmol each). 10.0 mg (0.018 mmol, 1.1% loading) of the complex Fe(P$^{Pr}$N$^H$N$^{Me}$)Br$_2$ was then added along with 0.040 mmol of NaBEt$_3$H as a toluene solution, and the reaction was stirred for 3 hours at 25° C. The reaction was quenched by exposure to air and the product mixture was analysed by NMR spectroscopy. Olefin Conversion=54%, IO: =54%.

Example J

In a nitrogen-filled drybox, a scintillation vial was charged with 143 mg (1.27 mmol) of 1-octene and 1.27 mmol of silane (234 mg, diphenylsilane). 5.0 mg (0.007 mmol, 1.1% loading) of the complex Fe(P$^{Ar}$N$^{Ph}$N)(CH$_2$SiMe$_3$)$_2$ was then added and the reaction was stirred for 2 hours at 50° C. The reaction was quenched by exposure to air and the product mixture was analysed by NMR spectroscopy. Olefin Conversion=>95%, AMP: =>95%.

Examples K and L

In a nitrogen-filled drybox, a J Young NMR tube was charged with 200 mg (1.78 mmol) of 1-octene and 1.78 mmol of silane (328 mg, diphenylsilane). 8.3 mg (0.013 mmol, 0.7% loading) of the complex Fe(P$^{Ar}$N$^{Ph}$N)Br$_2$ was then added along with 0.040 mmol of NaBEt$_3$H as a toluene solution and 0.2 mL of C$_6$D$_6$ and the reaction was stirred at room temperature. The reaction mixture was analysed by NMR spectroscopy. At 30 min AMP: 81% (Example K), at 2 hours AMP: >95% (Example L).

Example M

In a nitrogen-filled drybox, a scintillation vial was charged with 520 mg of a 1:1 mixture of 1-octene: HMTS (1.50 mmol each). 8.3 mg (0.013 mmol, 0.7% loading) of the complex Fe(P$^{Ar}$N$^{Ph}$N)Br$_2$ was then added along with 0.030 mmol of NaBEt$_3$H as a toluene solution and the reaction was stirred at 60° C. for 48 hours. The reaction mixture was quenched with air and analysed by NMR spectroscopy. Conversion=82%. AMP: 17%, IO: 61%.

The results of Examples A-I are summarized in Table 3:

TABLE 3

| Example -Activated Reaction Product With or Without Additional Ionic Activators | Silane | Loading | Temp | Time | AMP | MP | IO |
|---|---|---|---|---|---|---|---|
| Example A - Fe(P$^{Et}$N$^H$N)(CH$_2$SiMe$_3$)$_2$ | Ph$_2$SiH$_2$ | 2.2% | 50° C. | 2 hrs | 90 | | 8 |
| Example B - Fe(P$^{Et}$N$^H$N)(CH$_2$SiMe$_3$)$_2$ | Ph$_2$SiH$_2$ | 1.0% | 25° C. | 5 hrs | 42 | | |
| Example C - Fe(P$^{Et}$N$^H$N)(CH$_2$SiMe$_3$)$_2$ | Ph$_2$SiH$_2$ | 1.0% | 25° C. | 50 hrs | 70 | | |

TABLE 3-continued

| Example -Activated Reaction Product With or Without Additional Ionic Activators | Silane | Loading | Temp | Time | AMP | MP | IO |
|---|---|---|---|---|---|---|---|
| Example D - Fe(P$^{Et}$N$^{H}$N)(CH$_2$SiMe$_3$)$_2$ | HMTS | 1.0% | 50° C. | 2 hrs | | | >95% |
| Example E - Fe(P$^{Et}$N$^{H}$N)(CH$_2$SiMe$_3$)$_2$ | Et3SiH | 1.0% | 50° C. | 2 hrs | | | >95% |
| Example F - Co(P$^{Et}$N$^{H}$N)(CH$_2$SiMe$_3$)$_n$ | Ph$_2$SiH$_2$ | 0.3% | 25° C. | 16 hrs | 44 | 56 | |
| Example G - Co(P$^{Et}$N$^{H}$N)(CH$_2$SiMe$_3$)$_n$ | HMTS | 0.7% | 25° C. | 16 hrs | | | >95% |
| Example H - Co(P$^{Et}$N$^{H}$N)I$_2$ + NaBEtH$_3$ | HMTS | 0.8% | 25° C. | 3 hrs | | | >95% |
| Example I - Fe(P$^{Pr}$N$^{H}$N$^{Me}$)Br$_2$ + NaBEtH$_3$ | HMTS | 1.1% | 25° C. | 3 hrs | | | 54 |
| Example J - Fe(P$^{Ar}$N$^{Ph}$N)(CH$_2$SiMe$_3$)$_2$ | Ph$_2$SiH$_2$ | 1.1% | 50° C. | 2 hrs | >95% | | <5% |
| Example K - Fe(P$^{Ar}$N$^{Ph}$N)Br$_2$ + NaBEtH$_3$ | Ph$_2$SiH$_2$ | 0.7% | 25° C. | 30 min | 81% | | |
| Example L - Fe(P$^{Ar}$N$^{Ph}$N)Br$_2$ + NaBEtH$_3$ | Ph$_2$SiH$_2$ | 0.7% | 25° C. | 2 hrs | >95% | | |
| Example M - Fe(P$^{Ar}$N$^{Ph}$N)Br$_2$ + NaBEtH$_3$ | HMTS | 0.7% | 60° C. | 48 hrs | 17 | | 61 |

Example 5: Evaluation of Catalysts Loading and Reaction Kinetics on Hydrosilylation Reaction Catalyzed by Co(PNN)Cl$_2$ Activated System General procedure for catalysis using CoCl$_2$(PNpy): A substrate mixture containing 1-octene (11.2 g, 100 mmol), Ph$_2$SiH$_2$ (20.3 g, 110 mmol) and mesitylene (2 g, 16.67 mmol) was pre-made and used in small portions in the catalytic studies using the procedures described below. Catalytic reactions using 1 mol % loading: A scintillation vial was loaded with the cobalt complex (0.004 mmol), and the pre-made substrate mixture (134 mg, 100 equiv). To this stirring mixture was then added NaBEt$_3$H (0.01 mmol, 10 µL of a 1M solution in toluene). The red suspension immediately turned into a dark brown solution upon the addition of the NaBEt$_3$H. Aliquots were taken at certain time points, diluted with CDCl$_3$, and yields were determined by $^1$H NMR spectroscopy by integrating to mesitylene. Catalytic reactions using<0.5 mol % loading: For catalyst loadings<0.5 mol %, the activation of CoCl$_2$(PNpy) was slow, as indicated by the slow color evolution. In these cases, a scintillation vial was loaded with the cobalt complex (0.004 mmol), and the pre-made mixture (134 mg, 100 equiv). To this stirring mixture was then added NaBEt$_3$H (0.01 mmol, 10 µL of a 1M solution in toluene). The red suspension immediately turned into a dark brown solution upon the addition of the NaBEt$_3$H. After all the cobalt complex has been dissolved (ca. 1 min), this solution was immediately diluted with additional substrate mixture to the desired concentration (134 mg, 100 equiv). Aliquots were taken at certain time points, diluted with CDCl$_3$, and yields were determined by $^1$H NMR spectroscopy by integrating to mesitylene.

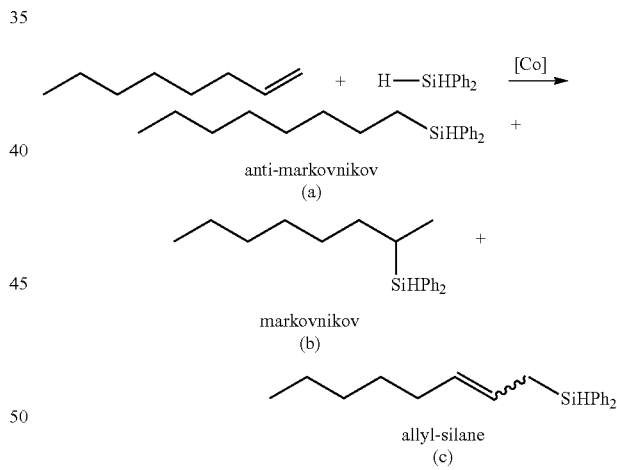

anti-markovnikov
(a)

markovnikov
(b)

allyl-silane
(c)

The results of Examples 1-5 are summarized in Table 4:

TABLE 4

| entry | [Co]$^a$ | loading | time | a (%)$^c$ | b (%)$^c$ | c (%)$^c$ | total (%)$^d$ |
|---|---|---|---|---|---|---|---|
| 1 | CoCl$_2$($^{iPr}$P$^{Pr}$N$^{H}$N) + 2.5NaBEt$_3$H | 0.5 mol % | 5 mins | >99 | 0 | 0 | >99 |
| 2 | CoCl$_2$(P$^{Pr}$N$^{Ph}$N)$^b$ + 2.5NaBEt$_3$H | 1 mol % | 2.5 h | 42 | 38 | 4 | 88 |
| 3 | CoCl$_2$(P$^{Ar}$N$^{Ph}$N) + 2.5NaBEt$_3$H | 0.5 mol % | 1 h | 46 | 43 | 5 | 99 |

TABLE 4-continued

| entry | [Co]$^a$ | loading | time | a (%)$^c$ | b (%)$^c$ | c (%)$^c$ | total (%)$^d$ |
|---|---|---|---|---|---|---|---|
| 4 | [CoCl(P$^{Et}$N$^H$N)]$_2$ + 2.5NaBEt$_3$H | 0.5 mol % | 48 h | 45 | 6 | 0 | 51 |
| 5 | [CoMe(P$^{Et}$N$^H$N)]$_2$ | 0.5 mol % | 48 h | 11 | >1 | 0 | 11 |

$^a$Conditions: 0.004 mmol [Co], 0.8 mmol 1-octene, 0.88 mmol Ph$_2$SiH$_2$, 25° C.
$^b$Conditions: 0.004 mmol [Co], 0.4 mmol 1-octene, 0.44 mmol Ph$_2$SiH$_2$, 25° C.
$^c$Yields were determined by integration of product Si—H resonances to mesitylene in the $^1$H NMR spectra of crude reaction mixtures.
$^d$Total conversions were determined by integration of 1-octene resonances to mesitylene in the $^1$H NMR spectra of crude reaction mixtures.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to a claim element in the singular, for example, using the articles "a," "an," "the" or "said," is not to be construed as limiting the element to the singular.

What is claimed is:

1. A reaction product comprising a ligand component according to formula (1):

$$R^1_2P-X-N=C(R^2)-Y \qquad (1),$$

wherein:
  $R^1$ is Ph or Cyc or a $C_1$-$C_{20}$ substituted or unsubstituted alkyl group;
  each Ph is a substituted or unsubstituted phenyl group;
  each Cyc is a substituted or unsubstituted cycloalkyl group;
  X is an unsubstituted arylene or a $C_2$-$C_3$ substituted or unsubstituted alkylene;
  $R^2$ is H, methyl or Ph; and
  Y is pyridyl or 6-phenylpyridyl or 6-methylpyridyl;
  with the proviso that when X is a $C_2$ substituted or unsubstituted alkylene and Y is pyridyl, $R^2$ is methyl or Ph; and
  a metal precursor according to formula (2):

$$[M\text{-}A_x]_n \qquad (2),$$

wherein:
  M is a metal selected from iron, cobalt, manganese, and ruthenium;
  each A is independently a displaceable substituent;
  subscript x is an integer with a value ranging from 1 to a maximum valence number of M; and
  n is 1 or 2,
  wherein the reaction product comprises a single phosphorus atom.

2. The reaction product of claim 1, wherein the metal precursor is selected from iron (II) bromide, cobalt (II) chloride, cobalt (I) chloride, Co (I) Me, and any combination thereof.

3. The reaction product according to claim 1, wherein the reaction product is further defined according to any one of formulas (2A), (2B), (2C), (2D), (2F), and (2G) as:

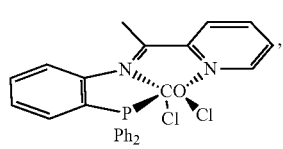
(2A)

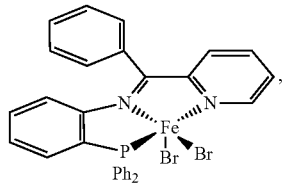
(2B)

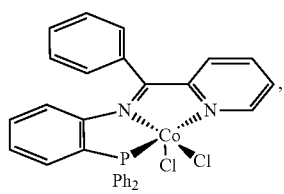
(2C)

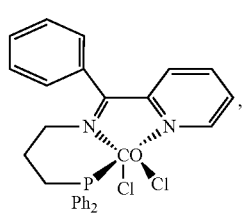
(2D)

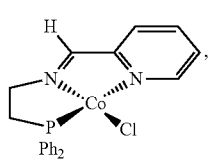
(2E)

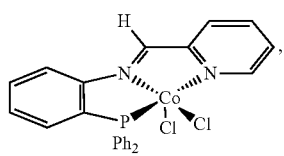
(2F) or

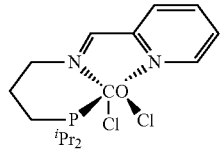
(2G)

wherein each Ph is an unsubstituted phenyl group.

4. An activated reaction product comprising the reaction product of claim 1 and an ionic activator or a reducing agent.

5. The activated reaction product of claim 4, wherein the ionic activator is LiCH$_2$SiMe$_3$.

6. A composition comprising:
(A) the activated reaction product according to claim 4;
(B) a compound having an average, per molecule, of one or more aliphatically unsaturated organic groups; and
optionally (C) an Si—H functional compound having an average, per molecule, of at least one silicon-bonded hydrogen atom, wherein component (C) is present when the compound of component (B) does not contain a silicon-bonded hydrogen atom.

7. The composition of claim 6, where:
compound (B) is a polyorganosiloxane having an average, per molecule, of one or more aliphatically unsaturated organic groups capable of undergoing hydrosilylation reaction;
compound (C) a silane according to formula (5):

wherein:
subscript e is 0, 1, 2, or 3; subscript f is 1, 2, 3, or 4, with the proviso that a sum of (e+f) is 4, and
each $R^4$ is independently a halogen atom or a monovalent organic group.

8. A method comprising:
(1) combining components comprising a metal precursor and a ligand component, thereby preparing a reaction product, where:
the metal precursor has formula (2): $[M\text{-}A_x]_n$, wherein M is a metal selected from iron, cobalt, manganese, and ruthenium; each A is independently a displaceable substituent; subscript x is an integer with a value ranging from 1 to a maximum valence number of M; and n is 1 or 2; and
the ligand component has general formula (1): $R^1{}_2P$—X—N=C($R^2$)—Y, wherein $R^1$ is Ph or Cyc or a $C_1$-$C_{20}$ substituted or unsubstituted alkyl group; each Ph is a substituted or unsubstituted phenyl group; each Cyc is a substituted or unsubstituted cycloalkyl group; X is an unsubstituted arylene or a $C_2$-$C_3$ substituted or unsubstituted alkylene; $R^2$ is H, methyl or Ph; and Y is pyridyl or 6-phenylpyridyl or 6-methylpyridyl; with the proviso that when X is a $C_2$ substituted or unsubstituted alkylene and Y is pyridyl, $R^2$ is methyl or Ph,
wherein the reaction product comprises a single phosphorus atom.

9. The method according to claim 8, wherein the reaction product is further defined according to any one of formulas (2A), (2B), (2C), (2D), (2F), and (2G) as:

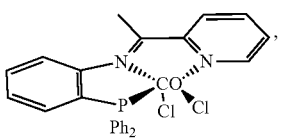

(2A)

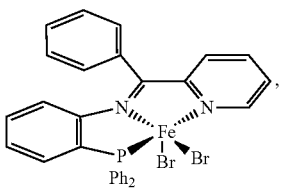

(2B)

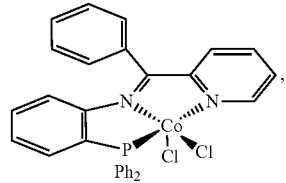

(2C)

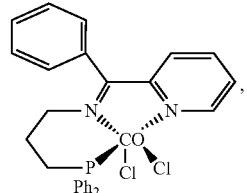

(2D)

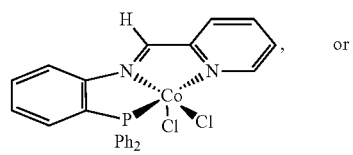

(2F)

or

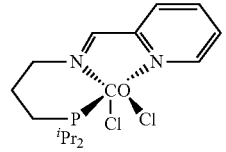

(2G)

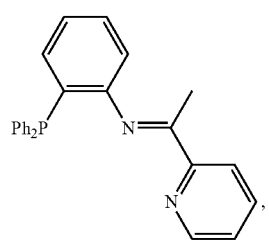

wherein each Ph is an unsubstituted phenyl group.

10. The method according to claim 8, wherein formula (1) is further defined according to any one of formulas (1A)-(1I) as:

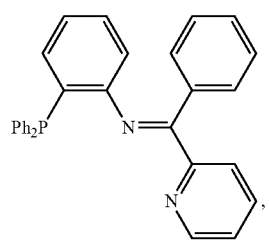

(1A)

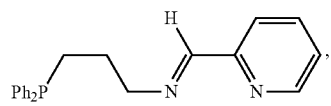

(1B)

(1C)

-continued

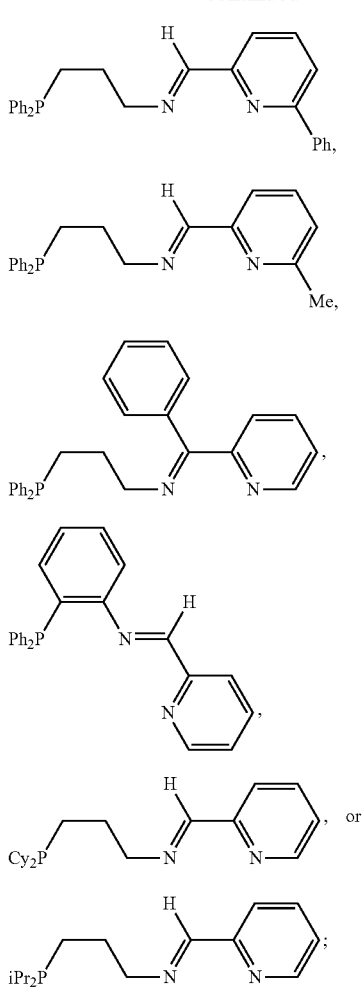

wherein each Ph is an unsubstituted phenyl group, wherein Cy is an unsubstituted cyclohexyl group and iPr is an isopropyl group.

11. The method according to claim 8, wherein the metal precursor is selected from iron (II) bromide, iron (II) chloride, cobalt (II) chloride, cobalt (I) chloride, Co (I) Me, and any combination thereof.

12. The method according to claim 8 further comprising (2) combining the reaction product with an ionic activator or a reducing agent to form an activated reaction product.

13. The method of claim 12, wherein the ionic activator is $LiCH_2SiMe_3$ or $LiCH_3$.

14. The composition of claim 6, where the composition further comprises one or more additional components, which are distinct from components (A), (B), and (C), and which are selected from the group consisting of (D) a spacer; (E) an extender, a plasticizer, or a combination thereof; (F) a filler; (G) a filler treating agent; (H) a biocide; (I) a stabilizer, (J) a flame retardant; (K) a surface modifier; (L) a chain lengthener; (M) an endblocker; (N) a flux agent; (O) an anti-aging additive; (P) a pigment; (Q) an acid acceptor; (R) a rheological additive; (S) a vehicle; (T) a surfactant; (U) a corrosion inhibitor; and a combination thereof.

15. A reaction product of the composition of claim 6.

16. A method comprising:

(1) combining components comprising a metal precursor and a ligand component, thereby preparing a reaction product (A), where:

the metal precursor has formula (2): $[M\text{-}A_x]_n$, wherein M is a metal selected from iron, cobalt, manganese, and ruthenium; each A is independently a displaceable substituent; subscript x is an integer with a value ranging from 1 to a maximum valence number of M; and n is 1 or 2; and the ligand component has general formula (1): $R^1_2P\text{—}X\text{—}N\text{=}C(R^2)\text{—}Y$, wherein $R^1$ is Ph or Cyc or a $C_1\text{-}C_{20}$ substituted or unsubstituted alkyl group; each Ph is a substituted or unsubstituted phenyl group; each Cyc is a substituted or unsubstituted cycloalkyl group; X is an unsubstituted arylene or a $C_2\text{-}C_3$ substituted or unsubstituted alkylene; $R^2$ is H, methyl or Ph; and Y is pyridyl or 6-phenylpyridyl or 6-methylpyridyl; with the proviso that when X is a $C_2$ substituted or unsubstituted alkylene and Y is pyridyl, $R^2$ is methyl or Ph;

(2) combining the prepared reaction product (A) with a composition comprising:

(B) a compound having an average, per molecule, of one or more aliphatically unsaturated organic groups; and optionally (C) an Si—H functional compound having an average, per molecule, of at least one silicon-bonded hydrogen atom, wherein component (C) is present when the compound of component (B) does not contain a silicon-bonded hydrogen atom;

(3) combining the reaction product with an ionic activator or a reducing agent to form an activated reaction product; and (4) reacting component (B) and optionally component (C) in the presence of the activated reaction product via a hydrosilylation reaction to form a reaction product of component (B) and optionally component (C).

17. The method of claim 16, the activated reaction product is formed in situ with component (B) and optional component (C).

18. The reaction product according to claim 2, wherein the reaction product is further defined according to any one of formulas (2A), (2B), (2C), (2D), (2F), and (2G) as:

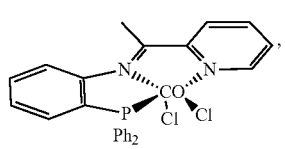 (2A)

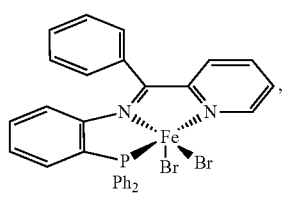 (2B)

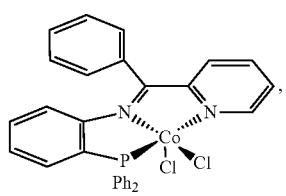 (2C)

-continued

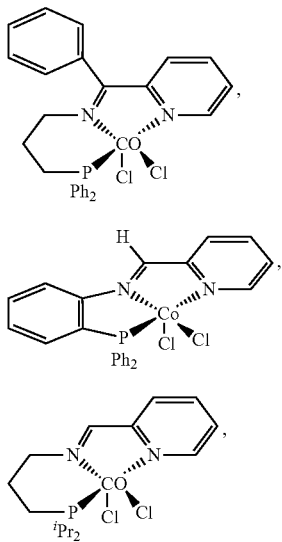

wherein each Ph is an unsubstituted phenyl group.

19. A reaction product comprising
a ligand component according to formula (1):

$$R^1{}_2P\text{—}X\text{—}N\text{=}C(R^2)\text{—}Y \qquad (1),$$

wherein:
$R^1$ is Ph or Cyc or a $C_1$-$C_{20}$ substituted or unsubstituted alkyl group;
each Ph is a substituted or unsubstituted phenyl group;
each Cyc is a substituted or unsubstituted cycloalkyl group;
X is an unsubstituted arylene or a $C_2$-$C_3$ substituted or unsubstituted alkylene;
$R^2$ is H, methyl or Ph; and
Y is pyridyl or 6-phenylpyridyl or 6-methylpyridyl;
with the proviso that when X is a $C_2$ substituted or unsubstituted alkylene and Y is pyridyl, $R^2$ is methyl or Ph; and a metal precursor according to formula (2):

$$[M\text{-}A_x]_n \qquad (2),$$

wherein:
M is nickel;
each A is independently a halogen atom or a monovalent organic group;
subscript x is an integer with a value ranging from 1 to a maximum valence number of M; and
n is 1 or 2,
wherein the reaction product includes a single phosphorus atom.

20. An activated reaction product comprising the reaction product of claim 19 and an ionic activator or a reducing agent.

21. The activated reaction product of claim 20, wherein the ionic activator is $LiCH_2SiMe_3$.

22. A composition comprising:
(A) the activated reaction product according to claim 20;
(B) a compound having an average, per molecule, of one or more aliphatically unsaturated organic groups; and
optionally (C) an Si—H functional compound having an average, per molecule, of at least one silicon-bonded hydrogen atom, wherein component (C) is present when the compound of component (B) does not contain a silicon-bonded hydrogen atom.

23. The composition of claim 22, where:
compound (B) is a polyorganosiloxane having an average, per molecule, of one or more aliphatically unsaturated organic groups capable of undergoing hydrosilylation reaction;
compound (C) a silane according to formula (5):

$$R^4{}_e SiH_f \qquad (5),$$

wherein:
subscript e is 0, 1, 2, or 3; subscript f is 1, 2, 3, or 4, with the proviso that a sum of (e+f) is 4, and
each $R^4$ is independently a halogen atom or a monovalent organic group.

* * * * *